US008822410B2

(12) United States Patent
Simons et al.

(10) Patent No.: US 8,822,410 B2
(45) Date of Patent: Sep. 2, 2014

(54) TYMPANIC MEMBRANE PERMEATING EAR DROPS AND USES THEREOF

(75) Inventors: Emmanuel John Simons, Somerville, MA (US); Todd R. Hoare, Ontario (CA); Daniel S. Kohane, Newton, MA (US); Robert S. Langer, Newton, MA (US)

(73) Assignees: Children's Medical Center Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 273 days.

(21) Appl. No.: 12/993,358

(22) PCT Filed: May 19, 2009

(86) PCT No.: PCT/US2009/003084
§ 371 (c)(1),
(2), (4) Date: Mar. 21, 2011

(87) PCT Pub. No.: WO2009/142719
PCT Pub. Date: Nov. 26, 2009

(65) Prior Publication Data
US 2011/0166060 A1    Jul. 7, 2011

Related U.S. Application Data

(60) Provisional application No. 61/054,339, filed on May 19, 2008.

(51) Int. Cl.
*A61K 38/12* (2006.01)
*A61K 31/7048* (2006.01)
*A61K 31/18* (2006.01)
*A61P 27/16* (2006.01)
*A61K 8/18* (2006.01)
*A61K 31/245* (2006.01)
*A61K 31/42* (2006.01)
*A61K 31/38* (2006.01)
*A61K 47/48* (2006.01)
*A61K 9/00* (2006.01)

(52) U.S. Cl.
CPC ......... *A61K 9/0046* (2013.01); *A61K 47/48046* (2013.01); *A61K 47/4823* (2013.01); *A61K 47/48784* (2013.01); *A61K 47/48023* (2013.01); Y10S 514/817 (2013.01)
USPC ............. 514/2.8; 514/2.4; 514/12.2; 514/817

(58) Field of Classification Search
CPC ................... A61K 47/48046; A61K 47/4823; A61K 9/0046; A61K 47/48023; A61K 47/48784
USPC .................. 514/2.8, 2.4, 12.2, 817
See application file for complete search history.

(56) References Cited

U.S. PATENT DOCUMENTS

| 4,206,757 A | 6/1980 | Grandadam et al. |
| 4,783,337 A | 11/1988 | Wong et al. |
| 5,684,051 A | 11/1997 | Thompson |
| 7,195,623 B2 | 3/2007 | Burroughs et al. |
| 2004/0101560 A1* | 5/2004 | Sawchuk et al. ............... 424/486 |
| 2005/0137189 A1* | 6/2005 | van Duzer et al. .......... 514/224.5 |
| 2007/0155715 A1 | 7/2007 | Van Duzer et al. |
| 2007/0238747 A1 | 10/2007 | Van Duzer et al. |
| 2007/0269379 A1* | 11/2007 | Mitragotri et al. .............. 424/9.2 |

OTHER PUBLICATIONS

J. Berger, Structure and interactions in chitosan hydrogels formed by complexation or aggregation for biomedical applications, 2004, European Journal of Pharmaceutics and Biopharmaceutics, 57, pp. 35-52.*
Luis Pardo, The neuronal lipid membrane permeability was markedly increased by bupivacaine and mildly affected by lidocaine and ropivacaine, 2002, European Journal of PHarmacology, 455, pp. 81-90.*
Josias Hamman, Chitosan Based Polyelectrolyte Complexes as Potential Carrier Materials in Drug Delivery Systems, Mar. 2010, Drugs, 8, pp. 1305-1322.*
International Search Report and Written Opinion for PCT/US2009/003084 mailed Aug. 24, 2009.
International Preliminary Report on Patentability for PCT/US2009/003084 mailed Dec. 2, 2010.
Alvarez-Román et al., Skin permeability enhancement by low frequency sonophoresis: lipid extraction and transport pathways. J Pharm Sci. Jun. 2003;92(6):1138-46.
Berman, Management of acute and chronic otitis media in pediatric practice. Curr Opin Pediatr. Oct. 1995;7(5):513-22.
Casselbrant et al., Genetic susceptibility to otitis media. Curr Opin Allergy Clin Immunol. Feb. 2005;5(1):1-4.
Casselbrant et al., The genetics of otitis media. Curr Allergy Asthma Rep. Jul. 2001;1(4):353-7.
Chen et al., Characterization of polyelectrolyte complexes between chondroitin sulfate and chitosan in the solid state. J Biomed Mater Res A. Oct. 1, 2005;75(1):128-37.
Choi et al., Effect of additives on the physicochemical properties of liquid suppository bases. Int J Pharm. Nov. 10, 1999;190(1):13-9.
Daly et al., Epidemiology, natural history, and risk factors: panel report from the Ninth International Research Conference on Otitis Media. Int J Pediatr Otorhinolaryngol. Mar. 2010;74(3):231-40. Epub Oct. 17, 2009.
Faden et al., Otitis media: back to basics. Pediatr Infect Dis J. Dec. 1998;17(12):1105-12; quiz 1112-3.

(Continued)

*Primary Examiner* — Julie Ha
*Assistant Examiner* — Erinne Dabkowski
(74) *Attorney, Agent, or Firm* — Wolf, Greenfield & Sacks, P.C.; C. Hunter Baker

(57) ABSTRACT

The present invention provides compositions and methods for noninvasive delivery of therapeutic agents across an intact tympanic membrane. For example, the compositions include a penetration enhancer which increases the flux of a therapeutic agent (e.g., antibiotic) across the tympanic membrane. Such compositions are particularly useful in the treatment of otitis media. Additionally, the composition may include a sustained release agents that, in some embodiments form sustained release reservoirs, in situ, once administered to a patient.

11 Claims, 28 Drawing Sheets

(56) References Cited

OTHER PUBLICATIONS

Freid et al., Ambulatory health care visits by children: principal diagnosis and place of visit. Vital Health Stat 13. May 1998;(137):1-23.

Hasegawa et al., Iontophoretic anaesthesia of the tympanic membrane. Clin Otolaryngol Allied Sci. Feb. 1978;3(1):63-6.

Hoffman et al., Tetracaine topical anesthesia for myringotomy. Laryngoscope. Sep. 2001;111(9):1636-8.

Karande et al., Design principles of chemical penetration enhancers for transdermal drug delivery. Proc Natl Acad Sci U S A. Mar. 29, 2005 29;102(13):4688-93. Epub Mar. 17, 2005.

Kasting et al., DC electrical properties of frozen, excised human skin. Pharm Res. Feb. 1990;7(2):134-43.

Kasting et al., Electrical analysis of fresh, excised human skin: a comparison with frozen skin. Pharm Res. Nov. 1990;7(11):1141-6.

Krueger et al., The development of a rat/human skin flap served by a defined and accessible vasculature on a congenitally athymic (nude) rat. Fundam Appl Toxicol. Dec. 1985;5(6 Pt 2):S112-21.

Kushner et al., Experimental demonstration of the existence of highly permeable localized transport regions in low-frequency sonophoresis. J Pharm Sci. Nov. 2004;93(11):2733-45.

Lanphear et al., Increasing prevalence of recurrent otitis media among children in the United States. Pediatrics. Mar. 1997;99(3):E1. 7 pages.

Lovdahl et al., Determination of ciprofloxacin levels in chinchilla middle ear effusion and plasma by high-performance liquid chromatography with fluorescence detection. J Chromatogr. Aug. 11, 1993;617(2):329-33.

Magnuson et al., Early structural changes in the rat tympanic membrane during pneumococcal otitis media. Eur Arch Otorhinolaryngol. 1994;251(7):393-8.

Merchant et al., Analysis of middle ear mechanics and application to diseased and reconstructed ears. Am J Otol. Mar. 1997;18(2):139-54.

Merchant et al., Middle ear mechanics of type IV and type V tympanoplasty: II. Clinical analysis and surgical implications. Am J Otol. Sep. 1995;16(5):565-75.

Morreale et al., Comparison of the antiinflammatory efficacy of chondroitin sulfate and diclofenac sodium in patients with knee osteoarthritis. J Rheumatol. Aug. 1996;23(8):1385-91.

Ronca et al., Anti-inflammatory activity of chondroitin sulfate. Osteoarthritis Cartilage. May 1998;6 Suppl A:14-21.

Rosowski et al., Cadaver middle ears as models for living ears: comparisons of middle ear input immittance. Ann Otol Rhinol Laryngol. May 1990;99(5 Pt 1):403-12.

Rosowski et al., Middle ear mechanics of type IV and type V tympanoplasty: I. Model analysis and predictions. Am J Otol. Sep. 1995;16(5):555-64.

Ruel-Gariépy et al., A thermosensitive chitosan-based hydrogel for the local delivery of paclitaxel. Eur J Pharm Biopharm. Jan. 2004;57(1):53-63.

Ruel-Gariépy et al., In situ-forming hydrogels—review of temperature-sensitive systems. Eur J Pharm Biopharm. Sep. 2004;58(2):409-26.

Ryu et al., Increased bioavailability of propranolol in rats by retaining thermally gelling liquid suppositories in the rectum. J Control Release. May 20, 1999;59(2):163-72.

Salyers et al., Cellular location of enzymes involved in chondroitin sulfate breakdown by *Bacteroides thetaiotaomicron*. J Bacteriol. Aug. 1980;143(2):772-80.

Takáts et al., Qualitative and quantitative determination of poloxamer surfactants by mass spectrometry. Rapid Commun Mass Spectrom. 2001;15(10):805-10.

Tang et al., Theoretical description of transdermal transport of hydrophilic permeants: application to low-frequency sonophoresis. J Pharm Sci. May 2001;90(5):545-68. J Pharm Sci. Oct. 2009;98(10):3878.

Teele et al., Epidemiology of otitis media during the first seven years of life in children in greater Boston: a prospective, cohort study. J Infect Dis. Jul. 1989;160(1):83-94.

Teele et al., Recent advances in otitis media. Epidemiology and natural history. Ann Otol Rhinol Laryngol Suppl. Apr. 1989;139:11-3.

Voss et al., Acoustic responses of the human middle ear. Hear Res. Dec. 2000;150(1-2):43-69.

Yong et al., Effect of sodium chloride on the gelation temperature, gel strength and bioadhesive force of poloxamer gels containing diclofenac sodium. Int J Pharm. Sep. 11, 2001;226(1-2):195-205.

* cited by examiner

TYMPANIC MEMBRANE PERMEATING EAR DROPS AND USES THEREOF

RELATED APPLICATIONS

The present application is a national stage filing under 35 U.S.C. § 371 of international application, PCT/US2009/003084, filed May 19, 2009, which claims priority under 35 U.S.C. § 119(e) to U.S. provisional patent application, U.S. Ser. No. 61/054,339, filed May 19, 2008, each of which is incorporated herein by reference.

GOVERNMENT SUPPORT

This invention was made with Government support under Grant No. R01 EB000351 awarded by the National Institutes of Health. The government has certain rights in this invention.

BACKGROUND

Between 90 and 95% of all U.S. children have at least one documented middle ear effusion by the age 2 [1, 2]. An estimated 20 million physician visits per year in the United States are attributed to otitis media ("OM" or middle ear infections) [3, 4]. OM is by definition inflammation of the middle ear, regardless of etiology or pathogenesis. Different forms of OM are most often differentiated by the presence of fluid (effusion) and by the duration or persistence of inflammation.

Present treatment of ear infections consists of systemic oral antibiotics, a treatment which requires multiple doses over 5-10 days and systemic exposure to antibiotics. The rise in antibiotic resistance, coupled with the many multifactorial etiology of OM pose difficulties in diagnosis and treatment of OM. Furthermore, current treatment presents a number of drawbacks including patient compliance issues due to gastrointestinal side effects, lack of effective drug concentration at the site of infection, and potential for opportunistic infections. Even after acute sign subside, generally within 72 hours, the root cause of the infection may persist for the remainder of the treatment, and beyond, even up to 2 months. Thus, making compliance with a physician's prescription important to prevent reoccurrence of infection.

Recurrence of disease is striking, with one third of all children in the U.S. having 6 or more episodes of AOM by age 7 [5]. Moreover, epidemiological studies suggest that the prevalence of recurrent OM among children, particularly infants, is on the rise [6]. Around the globe, the incidence of OM in children of other industrialized nations is similar to that in the U.S. In less developed countries, however, OM remains a significant cause of childhood mortality due to late-presenting intracranial complications.

The tympanic membrane is a barrier to the direct treatment of middle ear infections. Despite being thinnest layer of skin, it is still a barrier to trans-tympanic membrane diffusion. Therefore, the direct treatment of middle ear infections is problematic. The shortcomings of the current treatment of ear diseases such as middle ear infections suggest the need for a new treatment which is noninvasive, but also direct acting.

SUMMARY OF THE INVENTION

The present invention, in some aspects, provides a system for treating ear diseases. In particular, the present invention relates to noninvasive drug delivery systems for the delivery of a therapeutic agent across an intact tympanic membrane. In certain embodiments, the system provides sustained or extended release of the therapeutic agent. The inventive pharmaceutical compositions typically include a penetration enhancer (e.g., a surfactant, terpene) and a therapeutic agent (e.g., an antibiotic). The penetration enhancer is an agent that alters the stratum corneum of the tympanic membrane to allow for increased flux of the therapeutic agent across the tympanic membrane. The penetration enhancer provides for delivery of the therapeutic agent into the middle and/or inner ear of the subject. In various embodiments, for example, the penetration enhancer may include surfactants (anionic, cationic, nonionic, or zwitterionic surfactants), terpenes, amino amides, amino esters, azide-containing compounds, and alcohols. Therapeutic agents include agents that have a therapeutic benefit in the ear. In various aspects, for example, the therapeutic agents may include antibiotics, anti-inflammatory agents, anesthetics, analgesics, anti-fibrotics, and anti-sclerotics.

The pharmaceutical compositions may also optionally further include a sustained release drug delivery agent. As used herein, a sustained release drug delivery agent is a composition, e.g., a polymeric matrix, which provides a reservoir or vehicle for release of a therapeutic agent over an extended time in a subject, e.g., in a subject's ear canal. In some embodiments, a sustained release drug delivery agent is a material, such as, for example, a polyelectrolyte or thermo-responsive polymer, that undergoes a viscosity increase after being administered to a subject, e.g., administered into a subject's ear canal. It should be appreciated that the sustained release delivery agents of the invention include a variety of materials, including for example polymeric materials that form in response to temperature change (e.g., poloxamers), polyelectrolyte complexing (e.g., chitosan/chondroitin sulfate), polymer cross-linking (both physical and chemical, e.g., with rheological synergism or hyaluronic acid derivatives, respectively), or sensitivity to photo or electromagnetic waves (e.g., UV or microwaves), solvent exchange, or pH. In certain embodiments, the sustained release drug delivery agent is a hydrophilic material. In some embodiments, the sustained release drug delivery agent is a matrix-forming agent. Matrix forming agents are generally liquid at ambient conditions, however, once administered to a subject, the matrix forming agent gels (i.e., becomes more viscous). In various aspects, for example, the matrix forming agent changes viscosity once administered into a patient's ear canal forming in situ a reservoir in contact with or nearby the tympanic membrane. A reservoir in contact with the tympanic membrane maximizes exposure and concentration of the therapeutic agent at the surface of the tympanic membrane, thus increasing flux of the agent across the tympanic membrane and into the middle and/or inner ear. Exemplary matrix forming agents include polyelectrolyte complexes (e.g., chitosan-chondroitin complexes), thermo-responsive gelling agents (e.g., poloxamers), pre-polymers, alginates, un-crosslinked polymers, and monomers.

In other aspects, the present invention provides methods of using the inventive compositions. The inventive methods typically comprise administering the compositions into a subject's ear canal. In certain embodiments, the composition is administered so that the composition is in direct contact with the tympanic membrane of the subject. In certain embodiments, the composition will gel after administration to form a reservoir in the ear canal which is in contact with the tympanic membrane of the subject. In certain embodiments, the inventive compositions is used to treat otitis media in a subject.

In another aspect, the invention provides kits, which may additionally comprise any one or more of the following the composition in sterile packaging, containers for two-part matrix-forming agents, bottles and droppers for administration, instructions and prescribing information for administering the compositions contained therein. The kit may comprise one or more dosage units for administration to a subject.

In still other aspects, the invention provides pharmaceutical gel administration devices (e.g., multiple component syringes) for treating ear diseases. In other aspects, the invention provides pharmaceutical gel administration devices (e.g., multiple component syringes) for treating ear infections. In some embodiments, the pharmaceutical gel administration devices comprise a first compartment housing a solution comprising a cationic component of a matrix forming agent, a second compartment housing a solution comprising an anionic component of a matrix forming agent, optionally wherein the solution of the cationic component and/or the anionic component further comprises a therapeutic agent in an effective amount for treating the ear disease or infection, optionally wherein the solution of cationic component and/or the anionic component further comprises a penetration enhancer, a mixing chamber that is operable linked to the first compartment and the second compartment, a nozzle that is operable linked to the mixing chamber, and means for transferring the solutions of the first chamber and second chambers into the mixing chamber, to form a polyelectrolyte complex solution, and for transferring the polyelectrolyte complex solution out of the nozzle. It is to be understood that the pharmaceutical gel administration devices may have a variety of configurations. For example, in some embodiments, the pharmaceutical gel administration devices comprise additional compartments (e.g., a third compartment, a fourth compartment, etc.) housing additional compositions, such as for example compositions comprising a therapeutic agent or a penetration enhancer agent, or combinations thereof. In some embodiments, the pharmaceutical gel administration devices comprise a nozzle of physical dimensions suitable for entry into the external auditory canal of a subject, e.g., of a human infant or child, thereby facilitating administration, e.g., by a health provider or caregiver, of the pharmaceutical composition into the external auditory canal of the subject. The device may be for single or multiple uses.

Definitions

Animal: The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal.

Approximately or About: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

Biocompatible: As used herein, the term "biocompatible" refers to substances that are not toxic to cells. In some embodiments, a substance is considered to be "biocompatible" if its addition to cells in vivo does not induce inflammation and/or other adverse effects in vivo. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death.

Biodegradable: As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

Effective amount: In general, the "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient. For example, the effective amount of a compound with anti-proliferative activity is the amount that results in a sufficient concentration at the site of the tumor to kill or inhibit the growth of tumor cells. The effective amount of a compound used to treat infection is the amount needed to kill or prevent the growth of the organism(s) responsible for the infection.

In vitro: As used herein, the term "in vitro" refers to events that occur in an artificial environment, e.g., in a test tube or reaction vessel, in cell culture, etc., rather than within an organism (e.g. animal, plant, and/or microbe).

In vivo: As used herein, the term "in vivo" refers to events that occur within an organism (e.g. animal, plant, and/or microbe).

Suffering from: An individual who is "suffering from" a disease, disorder, and/or condition has been diagnosed with or displays one or more symptoms of the disease, disorder, and/or condition.

Treating: As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" a microbial infection may refer to inhibiting survival, growth, and/or spread of the microbe. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of an inventive vaccine nanocarrier to a subject.

Surfactant: As used herein, the term "surfactant" refers to any agent which preferentially absorbs to an interface between two immiscible phases, such as the interface between water and an organic solvent, a water/air interface, or an organic solvent/air interface. Surfactants usually possess a hydrophilic moiety and a hydrophobic moiety. Surfactants may also promote flux of a therapeutic or diagnostic agent across a biological membrane, e.g., a tympanic membrane.

Terpenes: As used herein, the term "terpene" refers to any agent derived, e.g., biosynthetically, or thought to be derived from unit(s) of isoprene (a five carbon unit). For example, isoprene units of terpenes may be linked together to form linear chains or they may be arranged to form rings. Typically, the terpenes disclosed herein promote flux of a therapeutic or diagnostic agent across a biological membrane, e.g., a tympanic membrane. Terpenes may be naturally derived or synthetically prepared.

DETAILED DESCRIPTION OF THE CERTAIN EMBODIMENTS OF THE INVENTION

Figure 1:
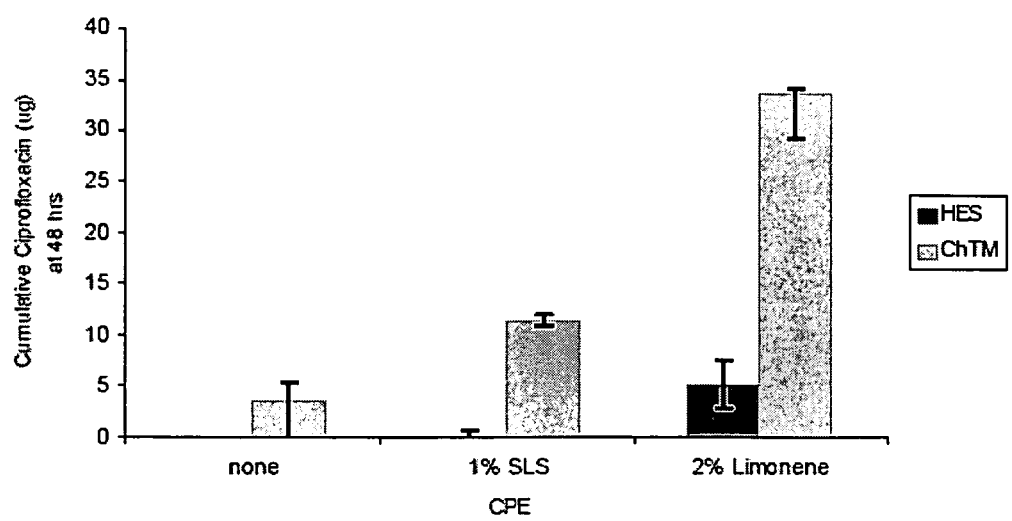
FIG. 1. Comparison of ciprofloxacin delivery across human epidermis with stratum corneum ("HES") and chinchilla tympanic membranes ("chTMs"). The two membranes showed similar relative sensitivity to 1% sodium lauryl sulfate and 2% limonene with respect to permeability to ciprofloxacin. Data are medians with 25th and 75th percentile error bars (n≥4).
Figure 2:
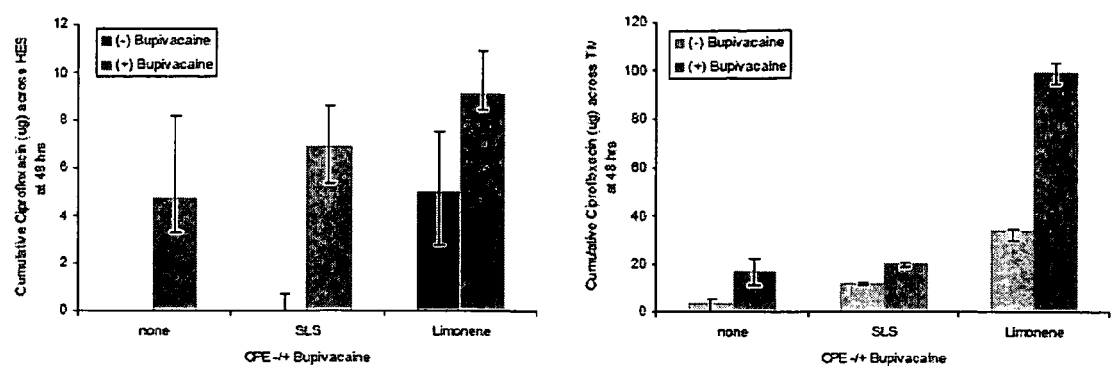
FIG. 2. Addition of bupivacaine (0.5%) to ciprofloxacin/chemical penetration enhancer ("CPE") mixtures resulted generally increased permeability tociprofloxacin. Data are medians with 25th and 75th percentile error bars (n≥4).
Figure 3:
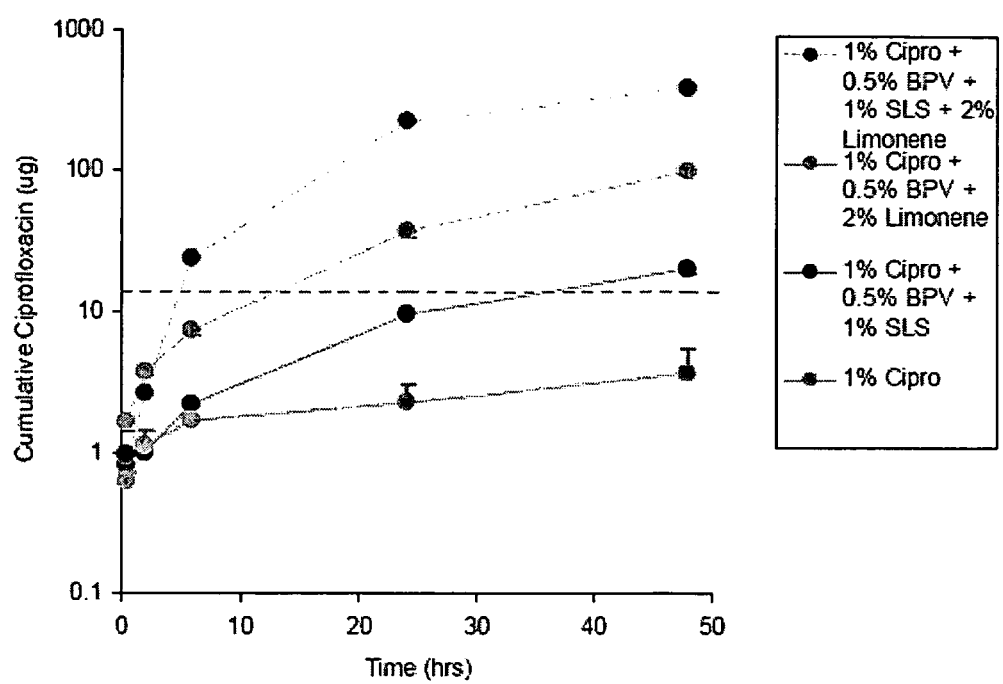
FIG. 3. Trans-tympanic membrane ("Trans-TM") ciprofloxacin differed considerably with CPE environment. All CPE combinations involving bupivacaine exceeded the target ciprofloxacin minimum inhibitory concentration ("MIC") (shown as dashed line), but did so on different time courses. Trans-TM ciprofloxacin flux in the absence of CPEs was non-zero, but failed to reach MIC-levels within 48 hours. Data are presented as medians (n≥4) with 25th and 75th percentile error bars (smaller than data point radius if not seen).
Figure 4:
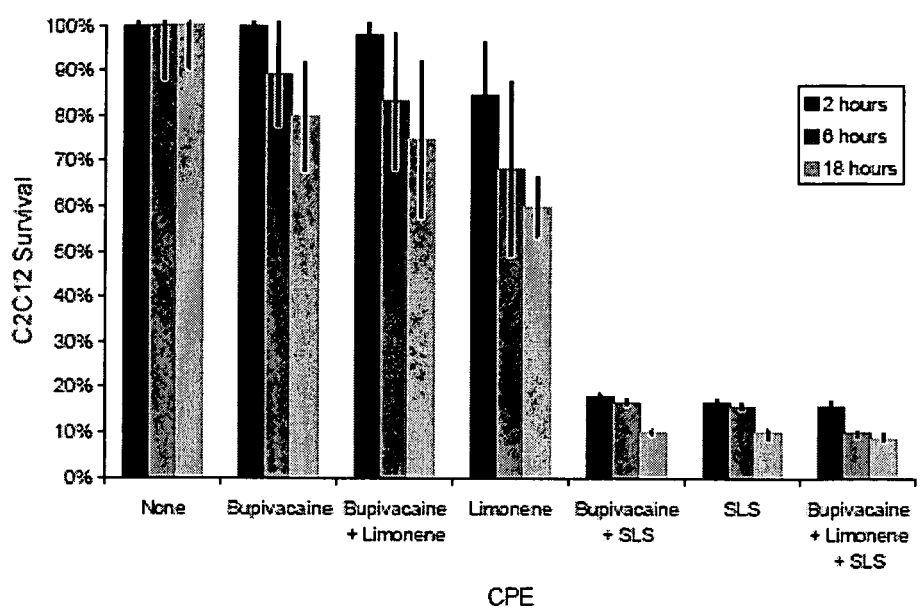
FIG. 4. C2C12 myoblast toxicity was nonexistent or minimal for all conditions except those involving sodium lauryl sulfate ("SLS"), which reduced cell viability by 80%, regardless of its combination with other CPEs. Limonene toxicity was small but significant at 6 and 18 hours, but not at 2 hours. The concentrations used were: bupivacaine (0.05%), limonene (0.2%), SLS (0.1%), regardless of whether applied alone or in combination. Values are means±standard deviations (n=8).
Figure 5:
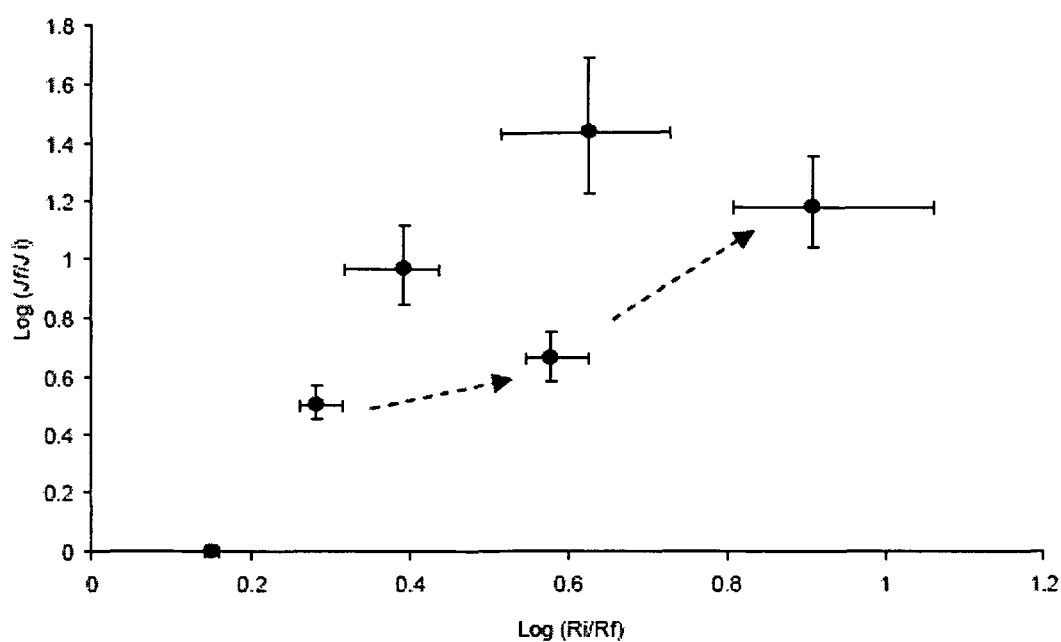
FIG. 5. Increased ciprofloxacin flux and, decreased tympanic membrane ("TM") resistance due to 48-hour exposure to single or combination CPEs. Each point represents median values obtained from TM populations (n≥4) treated with different CPE/ciprofloxacin mixtures. Dotted arrows point from a single CPE mixture (1% SLS) to one with 2 CPEs (1% SLS+0.5% bupivacaine), to one with 3 (1% SLS+0.5% bupivacaine+2% limonene).
Figure 6:
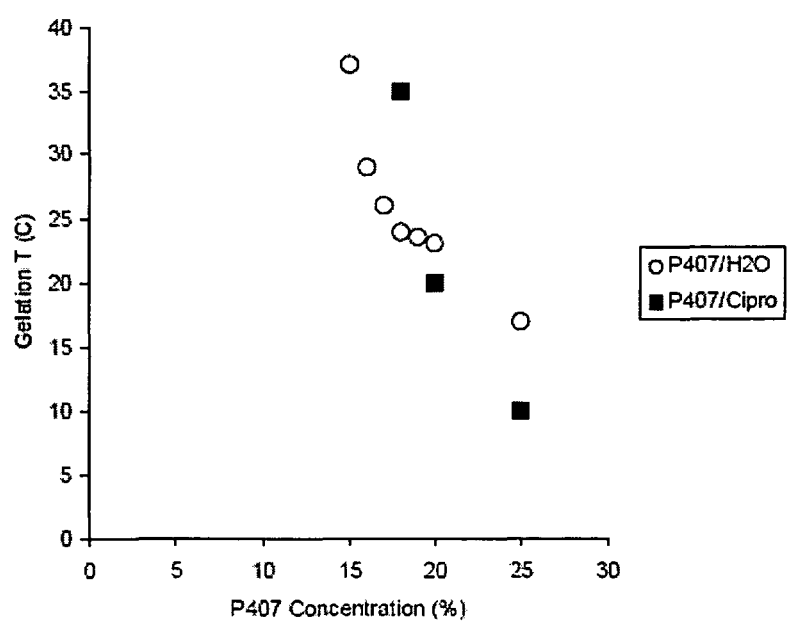
FIG. 6. Sol-gel transition temperature for increasing P407 concentrations prepared in dH2O and 1% ciprofloxacin solution. Average values shown with standard deviations (n=3, standard deviation error bars smaller than data points).
Figure 7:
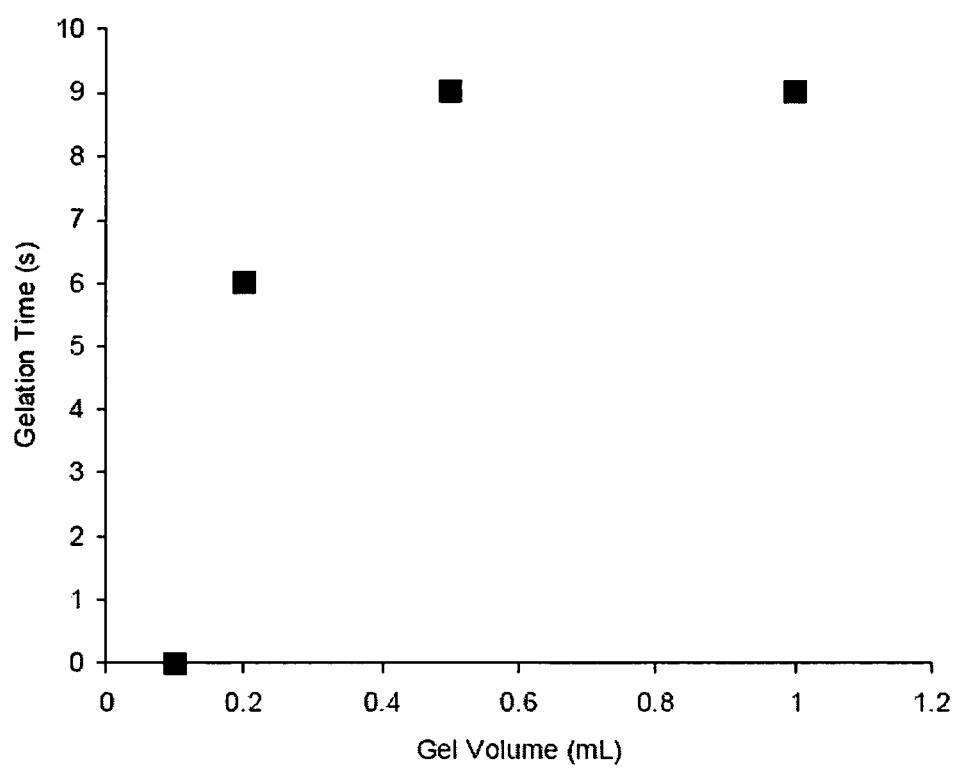
FIG. 7. Time required for 18% P407 in 1% ciprofloxacin solution to gel after transfer from 22 to 35° C. N=3 (standard deviation error bars smaller than data points).
Figure 8:
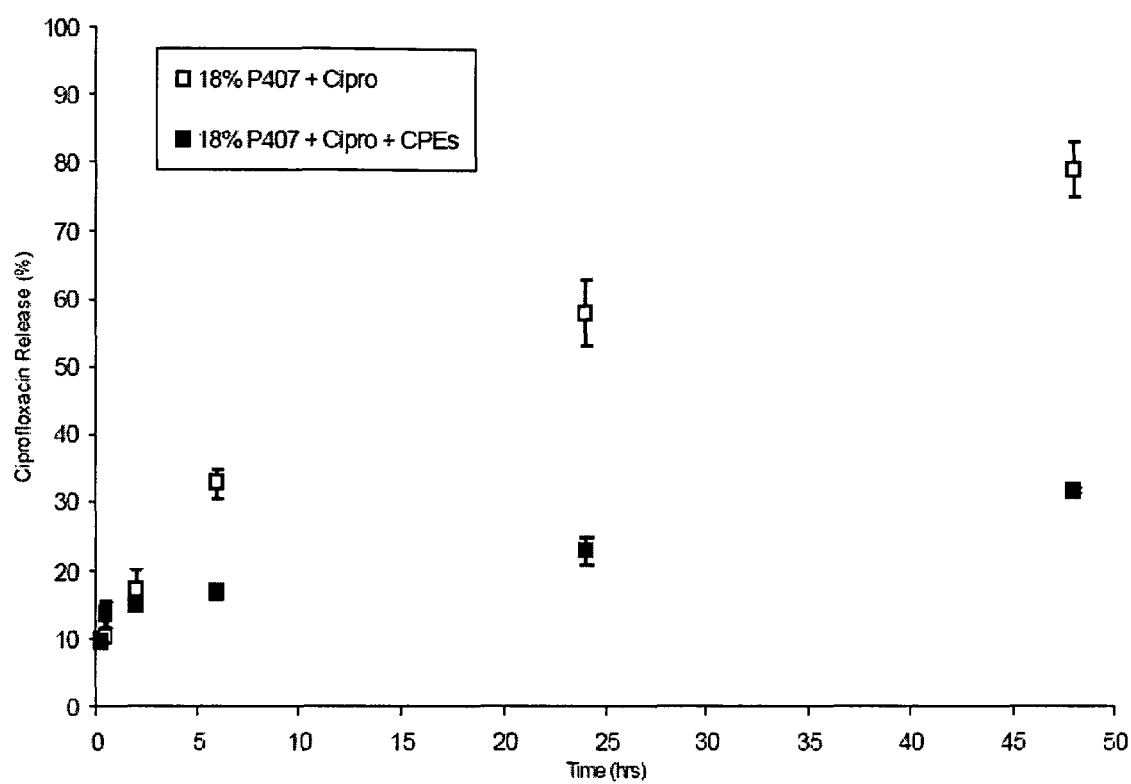
FIG. 8. Ciprofloxacin release from P407 hydrogels with and without chemical penetration enhancers (0.5% BPV+1% SLS). Percentages are calculated as the cumulative ciprofloxacin mass in the receiving chamber divided by the total original mass in the delivered mixture. Data are presented as means±standard deviations (n=8).
Figure 9:
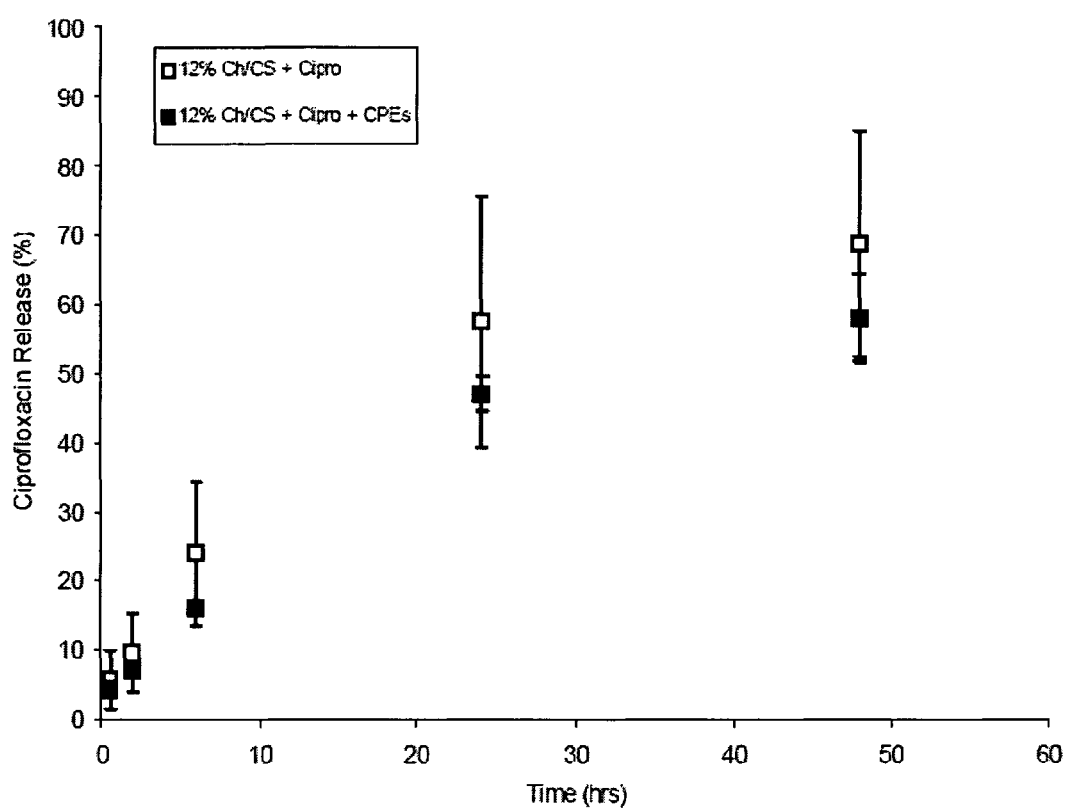
FIG. 9. Ciprofloxacin released from Ch/CS polyelectrolyte complexes into an aqueous receiving medium. Percentages are calculated as the cumulative ciprofloxacin mass in the receiving chamber divided by the total original mass in the delivery complex. Means±standard deviations are shown (n=8).
Figure 10:
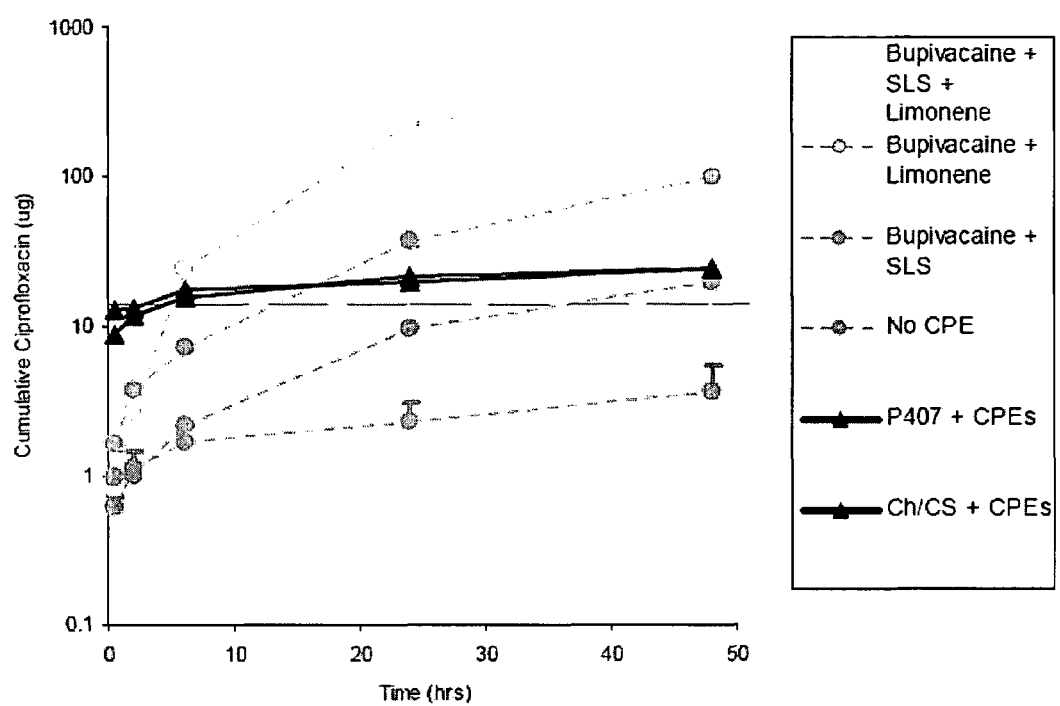
FIG. 10. Trans-TM ciprofloxacin delivery from P407 and Ch/CS gels compared to that from polymer-free mixtures. Both gels provide delivery of super-MIC ciprofloxacin levels (dashed line) within 12 hours of application, but steady-state rate of release is decreased compared to drug/CPE mixt FIG. 25. Bupivacaine release kinetics of polyelectrolyte complexes of chitosan of varying molecular weight (dissolved in acetic acid) and high molecular weight carboxymethyl cellulose (dissolved in water).

The present invention provides a drug delivery system for administering a therapeutic agent to the ear of a subject. The system provides for the efficient delivery of the agent to the middle and/or inner ear of the subject. The system includes compositions for delivery of a therapeutic agent across an intact tympanic membrane. In various aspects, the composition of the present invention comprises a combination of a penetration enhancer and a therapeutic agent. The composition may also optionally include a matrix forming agent. In various aspects, the invention comprise a single application composition for localized, sustained delivery of a therapeutic agent across the tympanic membrane. The inventive system is particularly useful in treating otitis media by providing sustained release and delivery of an antibiotic to the middle ear.
Compositions The inventive pharmaceutical compositions typically include a penetration enhancer (e.g., a surfactant, terpene) and a therapeutic agent (e.g., an antibiotic). The pharmaceutical compositions may also optionally further include a matrix-forming agent. The penetration enhancer is an agent that alters the stratum corneum of the tympanic membrane to increase the flux of the therapeutic agent across the tympanic membrane. The penetration enhancer facilitates delivery of the therapeutic agent into the middle and/or inner ear. Therapeutic agents include agents that have a therapeutic benefit in the ear. Matrix forming agents are generally liquid at ambient conditions, however, once administered to a subject, the matrix forming agent gels (i.e., becomes more viscous). In certain embodiments, the pharmaceutical composition does not substantially interfere with the hearing of the subject.
Penetration Enhancers Penetration enhancer refers to any agent that increases the flux of a therapeutic agent across the tympanic membrane. Penetration enhancers may include, but are not limited to, surfactants (anionic, cationic, nonionic, zwitterionic), terpenes, amino amides, amino esters, azide-containing compounds, and alcohols. In various aspects, the penetration enhancers may comprise between about 0.1 to about 10 percent of the composition. In various embodiments, the penetration enhancer may comprise between about 0.1 to about 1 percent of the composition, comprise between about 1 to about 2 percent of the composition, comprise between about 2 to about 3 percent of the composition, comprise between about 3 to about 4 percent of the composition, comprise between about 4 to about 5 percent of the composition, comprise between about 5 to about 6 percent of the composition, comprise between about 6 to about 7 percent of the composition, comprise between about 7 to about 8 percent of the composition, comprise between about 8 to about 9 percent of the composition, or comprise between about 9 to about 10 percent of the composition.

Surfactant penetration enhancers may include, but are not limited to, sodium dodecyl sulfate, ammonium lauryl sulfate, sodium laureth sulfate, cetyl trimethlammonium bromide, cetylpyridinium chloride, benzethonium chloride, cocamidopropyl betaine, cetyl alcohol, oleyl alcohol, octyl glucoside, decyl maltoside, sodium octyl sulfate, sodium decyl sulfate, sodium tetradecyl sulfate, sodium heptadecyl sulfate, sodium eicosyl sulfate, nicotine sulfate, sodium taurocholic sulfate, dimethyl sulfoxide, sodium tridecyl phosphate; decyldimethyl ammonio propane sulfonate, chembetaine oleyl, myristyldimethyl ammonio propane sulfonate; benzyl pyridinium chloride, dodecyl pyridinium chloride, cetyl pyridinium chloride, benzyldimethyl dodecyl ammonium chloride, benzyldimethyl dodecyl ammonium chloride, benzyldimethyl myristyl ammonium chloride, benzyldimethyl stearyl ammonium chloride, octyltrimethylammonium bromide, and dodecyltrimethylammonium bromide. In certain embodiments, the surfactant penetration enhancer is sodium dodecyl sulfate or sodium lauryl sulfate.

In various embodiments, any lipid including surfactants is suitable for use in making the inventive compositions. In certain embodiments, the lipid used in the invention composition is selected from the group consisting of phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid amides; sorbitan trioleate (Span 85) glycocholate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecylamine; acetyl palmitate; glycerol ricinoleate; hexadecyl sterate; isopropyl myristate; tyloxapol; poly(ethylene glycol)5000-phosphatidylethanolamine; and phospholipids. The lipid may be positively charged, negatively charged, or neutral. In certain embodiments, the lipid is a combination of lipids. Phospholipids useful in the inventive compositions include negatively charged phosphatidyl inositol, phosphatidyl serine, phosphatidyl glycerol, phosphatic acid, diphosphatidyl glycerol, poly(ethylene glycol)-phosphatidyl ethanolamine, dimyristoylphosphatidyl glycerol, dioleoylphosphatidyl glycerol, dilauryloylphosphatidyl glycerol, dipalmitotylphosphatidyl glycerol, distearyloylphosphatidyl glycerol, dimyristoyl phosphatic acid, dipalmitoyl phosphatic acid, dimyristoyl phosphitadyl serine, dipalmitoyl phosphatidyl serine, phosphatidyl serine, and mixtures thereof. Useful zwitterionic phospholipids include phosphatidyl choline, phosphatidyl ethanolamine, sphingomyeline, lecithin, lysolecithin, lysophatidylethanolamine, cerebrosides, dimyristoylphosphatidyl choline, dipalmitotylphosphatidyl choline, distearyloylphosphatidyl choline, dielaidoylphosphatidyl choline, dioleoylphosphatidyl choline, dilauryloylphosphatidyl choline, 1-myristoyl-2-palmitoyl phosphatidyl choline, 1-palmitoyl-2-myristoyl phosphatidyl choline, 1-palmitoyl-phosphatidyl choline, 1-stearoyl-2-palmitoyl phosphatidyl choline, dimyristoyl phosphatidyl ethanolamine, dipalmitoyl phosphatidyl ethanolamine, brain sphingomyelin, dipalmitoyl sphingomyelin, distearoyl sphingomyelin, and mixtures thereof. Zwitterionic phospholipids constitute any phospholipid with ionizable groups where the net charge is zero. In certain embodiments, the lipid is phosphatidyl choline.

Exemplary surfactants useful in the present invention include sodium dioctyl sulfo succinate, sodium dodecyl sulfate, cocoamidopropyl betaine, and sodium laureth sulfate, alkyl and alkyl ether sulfates (e.g., sodium coconut alkyl triethylene glycol ether sulfate; lithium tallow alkyl triethylene glycol ether sulfate; sodium tallow alkyl hexaoxyethylene sulfate), succinamates, sulfosuccinamates (e.g., disodium N-octadecyl-sulfosuccinamate, tetrasodium N-(1,2-dicarboxyethyl)-N-octadecylsulfosuccinamate, diamyl ester of sodium sulfosuccinic acid, dihexyl ester of sodium sulfosuccinic acid, dioctyl esters of sodium sulfosuccinic acid), olefin sulfonates, hydroxy-alkanesulfonates, beta-alkyloxy alkane sulfonates (e.g., potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium β-methoxyoctadecysulfonate, ammonium β-n-propoxydodecylsulfonate), dioctyl esters of sodium sulfosuccinic acid, alkyl ethoxylated sulfates, alkyl sulfates, aliphatic secondary and tertiary amines (e.g., sodium 3-dodecylaminopropionate, N-alkyltaurines, stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O) stearylamine, dihydroxy ethyl stearylamine, and arachidylbehenylamine), alkyl amphoglycinates (e.g., cocoamphoglycinate, lauroamphocarboxyglycinate, cocoamphocarboxyglycinate); alkyl amphopropionates (e.g., isostearoamphopropionate, cocoamphocarboxypropionic acid); alkyl ethoxylated sulfates; alkyl sulfates; aliphatic quaternary ammonium compounds (e.g., tallow propane diammonium dichloride, dialkyldimethylammonium chlorides, ditallowedimethyl ammonium chloride, ditallowedimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, and di(coconutalkyl benzyl ammonium chloride); aliphatic phosphonium compounds, aliphatic sulfonium compounds, alkyl amino sulfonates, alkyl betaines (e.g., coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine), sulfo betaines (e.g., coco dimethyl sulfopropyl betaine, stearyl dimethyl sulfopropyl betaine, lauryl dimethyl sulfoethyl betaine, lauryl bis(2-hydroxyethyl) sulfopropyl betaine), alkyl amido betaines, 4-[N,N-di(2-hydroxyethyl)-N-octadecylammonio]-butane-1-carboxylate; 5-[S-3-hydroxypropyl-S-hexadecylsulfonio]-3-hydroxy-pentanel-sulfate; 3-[P,P-diethyl-P-3,6,9-trioxatetradexoxylphosphonio]-2-hydroxy-propane-1-phosphate; 3-[N,N-dipropyl-N-3-dodecoxy-2-hydroxypropylammonio]-propane-1-phosphate; 3-(N,N-dimethyl-N-hexadecylammonio) propane-1-sulfonate; 3-(N,N-dimethyl-N-hexadecylammonio)-2-hydroxy-propane-1-sulfonate; 4-[N, N-di-(2-hydroxy-ethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and 5-[N,N-di (3-hydroxypropyl)-N-hexadecylammonio]-2-hydroxypentane-1-sulfate, sodium 3-dodecylaminopropane sulfonate; alkyl amphosulfonates; alkyl amphosulfosuccinates; oleoamphopropylsulfonate, and cocoamphopropylsulfonate; polyethylene oxide condensates; long chain tertiary phosphine oxides; long chain dialkyl sulfoxides; Silicone copolyols (e.g., dimethicone copolyols), stearamide diethanolamide (DEA), cocamide monoethanolamide (MEA), glyceryl monoleate, sucrose stearate, Cetheth-2, Poloxamer 181, hydrogenated tallow amide DEA, polyoxyethylene 4 sorbitol beeswax derivative (ATLAS 6-1702), polyoxyethylene 2 cetyl ether (BRIJ 52), polyoxyethylene 2 stearyl ether (BRIJ 72), polyoxyethylene 2 oleyl ether (BRIJ 92), polyoxyethylene 2 oleyl ether (BRIJ 93), sorbitan monopalmitate (SPAN 40), sorbitan monostearate (SPAN 60), sorbitan tristearate (SPAN 65), sorbitan monoleate, NF (SPAN 80) sorbitan trioleate (SPAN 85), fluorinated alkyl quaternary ammonium iodide; mixed mono- and bis-perfluoroalkyl phosphates, ammonium salts; mixed mono- and bis-fluoroalkyl phosphate, ammonium salts, complexed with aliphatic quaternary methosulfates; perfluoroalkyl sulfonic acid, ammonium salts; mixed telomer phosphate diethanolamine salts; amine perfluoroalkyl sulfonates; ammonium perfluoroalkyl sulfonates; potassium perfluoroalkyl sulfonates; potassium fluorinated alkyl carboxylates; ammonium perfluoroalkyl sulfonates; and ammonium perfluoroalkyl carboxylates; sodium dioctyl sulfosuccinate; magnesium dioctyl sulfosuccinate; ammonium dioctyl sulfosuccinate; magnesium dodecyl sulfate; ammonium dodecyl sulfate; cocoamidopropyl betaine sodium dinonyl sulfo succinate; sodium alpha olefin sulfonate; sodium laureth sulfate; magnesium laureth sulfate; ammonium laureth sulfate; cocoamidopropyl betaine; polyethoxylated glycol ether of glyceryl isostewarate; polyethoxylated glycol ether of glyceryl monooleate; PEG-30 glyceryl isostearate; polyoxyethylene glycerol monoleate; polyethylene glycol; PPG-18; PPG-10; 18 dimethicone; 1 dimethicon; cetyl polyethylene glycol; glyceryl monostearate; laureth-23; and PEG 75 lanolin. In certain embodiments, the surfactant is a silicon-containing chemical compound. Exemplary silicon-based detergents, emulsifiers, or surfactants useful in cosmetic compositions include dimethicone, cyclopentasiloxane, cyclohexasiloxane, PEG/dimethicone copolymers, PPG/dimethicone copolymers, phenyltrimethicone, alkyl silicones, amodimethicone, silicone quaternium-18, and dimethiconol.

Terpene penetration enhancers may include, but are not limited to, limonene, cymene, pinene, camphor, menthol, comphone, phellandrine, sabinene, terpinene, borneol, cineole, geraniol, linalol, pipertone, terpineol, eugenol, eugenol acetate, safrole, benzyl benzoate, humulene, beta-caryophyllene, eucakytol, hexanoic acid, octanoic acid, decanoic acid, undecanoic acid, dodecanoic acid, tridecanoic acid, myristic acid, palmitic acid, stearic acid, oleic acid, linoleic acid, linolenic acid, cholic acid; ethyl undecanoate, methyl laurate, methyl myristate, isopropyl myristate, isopropyl palmitate, palmityl palmitate, diethyl sebaccate, glyceryl monolaurate, glyceryl monooleate, and ethylpiperazine carboxylate. Any terpene or terpeniod compound may be used as a penetration enhancer in the inventive compositions. In certain embodiments, the penetration enhancer is limonene.

Alcohol penetration enhancers may include, but are not limited to, methanol, ethanol, propanol, isopropanol, butanol, isobutyl alcohol, and tert-amyl alcohol. In certain embodiments, the penetration enhancer is a compound with more than one hydroxyl group (e.g., glycerol). For example, the penetration enhancer may contain two, three, four, five, or more hydroxyl groups. In certain embodiments, the penetration enhancer is a hydroxyl-containing polymer.

Matrix Forming Agents

In various embodiments the present inventions comprise a sustained release formulation. In various aspects, sustained release of either the penetration enhancer and/or the therapeutic agent can be at a constant rate to deliver an effective amount of either the penetration enhancer or therapeutic agent to the surface of the tympanic membrane, the middle ear, or the inner ear. In various embodiments, the sustained release maybe at a constant rate over about 1 day, about 2 days, about 3 days, about 4 days, about 5 days, about 6 days, or about 7 days. In various embodiments, the sustained release maybe at a constant rate over a range of about 7 to about 10 days. In various embodiments, the sustained release may be at a constant rate over a range of about 7 days to about 14 days. In various embodiments, the sustained release may be at a constant rate over a range of about 14 to about 21 days. In various embodiments, the sustained release may be at a constant rate over a range of about 21 to about 30 days.

In various aspects, the sustained release profile is obtained by the addition of a matrix-forming agent to the composition. In various embodiments of the present inventions the composition may further comprise a matrix forming agent. In various embodiments, the matrix forming agents may undergo a change in viscosity, in situ, based on a phase change, a change in solubility, evaporation of a solvent, or mixing of components comprising the matrix forming agent. Such matrix forming agents gel, in situ after administration into a patient's ear canal to form a reservoir containing the therapeutic agent and penetration enhancer, allowing a sustained release of the therapeutic agent. Such a reservoir maintains contact with the tympanic membrane increasing the time for the therapeutic agent to permeate the tympanic membrane, and be delivered to the middle or inner ear. Such a reservoir maximizes exposure of the tympanic membrane to penetration enhancers and the therapeutic agent.

The matrix forming agent may be a polymer. The polymer may be a natural or synthetic polymer. In certain embodiments, the matrix forming agent is a hydrogel. Matrix forming agents may include, but are not limited to, polyelectrolyte complexes, thermo-responsive gelling agents, pre-polymers, alginates, un-crosslinked polymers, and monomers. Pre-polymers include low molecular weight molecules (e.g., oligomers) that are capable of polymerization and/or cross-linking. Matrix forming agents may further include biocompatible agents. Matrix forming agents may further include biodegradable agents. In certain embodiments the matrix forming agent is degraded and extruded from the body of a patient within 3 days of application, within 7 days of application, with 10 days of application, or within 14 days of application. In various embodiments of the present inventions, the matrix-forming agent has little or no effect on hearing threshold when applied into a subject's ear canal. In various aspects, the matrix-forming agents may comprise between about 0 to about 40 percent of the composition. In various embodiments, the matrix-forming agents may comprise between about 0 to about 10 percent of the composition, comprise between about 10 to about 20 percent of the composition, comprise between about 20 to about 30 percent of the composition, comprise between about 30 to about 40 percent of the composition, or comprise between about 40 to about 50 percent of the composition.

In various embodiments of the present inventions the polyelectrolyte complex may include, but is not limited to a, chitosan-chondroitin sulfate complex, gelatin, carboxymethycellulose, glycosaminoglycans and poly(vinyl alcohol). In various aspects, the relative ratios of chiosan to chondroitin sulfate may be between about 1:0.09 to about 1:1.4. In certain embodiments, the polyelectrolyte complex is a chitosan-chondroitin sulfate complex.

In various aspects the present inventions, the thermo-responsive gelling agent may include, but is not limited to, poly-ethylene oxide/polypropylene oxide based systems, poloxamers, poloxamer 407, poloxamer 188, poloxamines, methylcellulose, hydroxypropyl methylcellulose, ethyl (hydroxy ethyl) cellulose, xyloglucan, celluose acetate phthalate latex, poly (acrylic acid), N-isopropylacrylamide-based systems, thermoresponsive polysaccharides (including cellulose derivatives, chitosan, dextran and gellan gum. In certain embodiments, the thermo-responsive gelling agent is poloxamer 407.

Therapeutic Agents

A therapeutic agent can be any agent used to treat any ear disease, or symptom of an ear disease. Therapeutic agents may include, but are not limited to, antibiotics, anesthetics, anti-inflamatories, analgesics, anti-fibrotics, anti-sclerotics, anticoagulants, and diagnostic agents. In various aspects, the therapeutic agents may comprise between about 0.01 to about 10 percent of the composition. In various embodiments, the therapeutic agents may comprise between about 0.01 to about 1 percent of the composition, comprise between about 1 percent to about 2 percent of the composition, comprise between about 2 percent to about 3 percent of the composition, comprise between about 3 percent to about 4 percent of the composition, comprise between about 4 percent to about 5 percent of the composition, comprise between about 5 percent to about 6 percent of the composition, comprise between about 6 percent to about 7 percent of the composition, comprise between about 7 percent to about 8 percent of the composition, comprise between about 8 percent to about 9 percent of the composition, or comprise between about 9 percent to about 10 percent of the composition.

The exact amount required will vary from subject to subject, depending on the species, age, and general condition of the subject, the particular compound, its mode of administration, its mode of activity, condition being treated, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, the therapeutic agent is an antibiotic. Any antibiotic may be used in the inventive system. In certain embodiments the antibiotic is approved for use in humans or other animals. In certain embodiments the antibiotic is approved for use by the U.S. Food & Drug Administration. In certain embodiments, the antibiotic may be selected from the group consisting of cephalosporins, quinolones, polypeptides, macrolides, penicillins, and sulfonamides. Exemplary antibiotics may include, but are not limited to, ciprofloxacin, cefuroxime, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, enoxacin, gatifloxacin, levofloxacin, lomefloxacin, moxifloxacin, norfloxacin, ofloxacin, trovafloxacin, bacitracin, colistin, polymyxin B, azithromycin, clarithromycin, dirithromycin, erythromycin, roxithromycin, troleandomycin, telithromycin, spectinomycin, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, mafenide, sulfacetamide, sulfamethizole, sulfasalazine, sulfisoxazole, trimethoprim, and trimethoprim-sulfamethoxazole. In certain embodiments, the antibiotic is ciprofloxacin.

In certain embodiments, the therapeutic agent is an anesthetic. Any anesthetic may be used in the inventive system. In certain embodiments the anesthetic is approved for use in humans or other animals. In certain embodiments the anesthetic is approved for use by the U.S. Food & Drug Administration. Exemplary anesthetics may included, but are not limited to bupivicaine, tetracaine, procaine, proparacaine, propoxycaine, dimethocaine, cyclomethycaine, chloroprocaine, benzocaine, lidocaine, prilocaln, levobupivicaine, ropivacaine, dibucaine, articaine, carticaine, etidocaine, mepivacaine, piperocaine, and trimecaine. In certain embodiments, the anesthetic is bupivicaine.

In certain embodiments, the therapeutic agent is an anti-inflammatory agent. The anti-inflammatory agent may be a non-steroidal anti-inflammatory agent or a steroidal anti-inflammatory agent. Exemplary anti-inflammatory agents may include, but are not limited to, acetylsalicylic acid, amoxiprin, benorylate/benorilate, choline magnesium salicylate, diflunisal, ethenzamide, faislamine, methyl salicylate, magnesium salicylate, salicyl salicylate, salicylamide, diclofenac, aceclofenac, acemetacin, alclofenac, bromfenac, etodolac, indometacin, nabumetone, oxametacin, proglumetacin, sulindac, tolmetin, ibuprofen, alminoprofen, benoxaprofen, carprofen, dexibuprofen, dexketoprofen, fenbufen, fenoprofen, flunoxaprofen, flurbiprofen, ibuproxam, indoprofen, ketoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, oxyphenbutazone, phenazone, phenylbutazone, sulfinpyrazone, piroxicam, droxicam, lornoxicam, meloxicam, tenoxicam, hydrocortisone, cortisone acetate, prednisone, prednisolone, methylprednisolone, dexamethasone, betamethasone, triamcinolone, beclometasone, fludrocortisone acetate, deoxycorticosterone acetate, and aldosterone.

In various embodiments of the present inventions, combinations of various penetration enhancers and therapeutic agents have been observed to have a synergistic and heightened efficacy. In various aspects, such combinations may include, but are not limited to ciprofloxacin and limonene. In various aspects, such combinations may include, but are not limited to, ciprofloxacin and sodium dodecyl sulfate. In various aspects such combinations may include, but are not limited to, sodium dodecyl sulfate, limonene, bupivicaine and ciprofloxacin. In various aspects, such combination may include, but are not limited to sodium dodecyl sulfate, limonene and ciprofloxacin.

This invention also provides a pharmaceutical preparation comprising at least one of the compounds as described herein, or a pharmaceutically acceptable derivative thereof. In certain embodiments, the pharmaceutical composition includes a combination of therapeutic agents. For example, in certain embodiments, the composition includes an antibiotic and an anti-inflammatory agent. In other embodiments, the composition includes an antibiotic and an anesthetic. In certain embodiments, the composition includes more than one antibiotic. Furthermore, after formulation with an appropriate pharmaceutically acceptable carrier in a desired dosage, the pharmaceutical compositions of this invention can be administered to humans and other animals.

Dosage forms include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the compositions can also include adjuvants such as wetting agents, emulsifying and suspending agents, and perfuming agents. In certain embodiments, the compounds of the invention are mixed with solubilizing agents such an Cremophor, alcohols, oils, modified oils, glycols, polysorbates, cyclodextrins, polymers, and combinations thereof.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

Uses

Methods of using the various embodiments of the claimed invention are generally directed to methods of treating an ear disease. In various aspects, the compositions of the claimed invention may be used to deliver therapeutic or diagnostic agents across the tympanic membrane. Therefore, the compositions are particularly useful in treating diseases of the middle and/or inner ear.

In various aspects, the claimed inventive methods can be used to treat ear diseases, including, but not limited to, ear infections, development of fibroids in the middle ear, and otosclerosis. In various other aspects, the present invention may treat vertigo, Meniere's disease, mastoiditis, cholesteatoma, labryrinthitis, perilymph fistula, and superior canal dehiscence syndrome. In some embodiments, the methods disclosed herein are used for treating otitis media (OM). Different forms of OM, which may be treated by the methods disclosed herein, may be differentiated by the presence of fluid (effusion) and/or by the duration or persistence of inflammation. Effusions, if present, can be of any consistency, from water-like (serous) to viscid and mucous-like (mucoid), to pus-like (purulent); duration is classified as acute, subacute, or chronic. OM with effusion (OME) indicates inflammation with middle ear fluid (MEF), but in the absence of any indications of acute infection. Acute OM (AOM), with or without effusion, is characterized by rapid onset of the signs and symptoms associated with acute infection in the middle ear (e.g., otalgia, fever). In some embodiments, the methods are used for treating otitis media associated with infection by any of a number of pathogenic bacteria, including, for example, *Streptococcus pneumoniae, Haemophilus influenzae*, and *Moraxella catarrhalis*.

In various embodiments, administration of the inventive compositions consists of applying the composition into a subject's ear canal. A subject for treatment can be any mammal in need of treatment. In various aspects, the composition is in direct contact with the tympanic membrane for about 1 day to about 30 days. In various aspects, the composition is in contact with the tympanic membrane from about 1 day to about 3 days, from about 3 days to about 7 days, from about 7 days to about 14 days, from about 14 days to about 21 days, or from about 21 days to about 30 days. In various embodiments of the present inventions, the composition forms a sustained release reservoir, in contact with the tympanic membrane. In various aspects, the composition is applied into the ear canal as a liquid, and the composition gels in situ on the surface of the tympanic membrane. When in contact with the tympanic membrane, the therapeutic agent penetrates the tympanic membrane and is delivered to the middle ear. In various embodiments, the delivery across the tympanic membrane is a sustained release of the therapeutic agent over a number of days. The numbers of days that the composition can be in contact with the tympanic membrane can be, but is not limited to, 5 days, 7 days, 10 days, 14 days, 21 days, or 30 days. The composition may be applied singly, or repeatedly in the course of treatment. In various aspects, the composition may be periodically administered from about every 1 day to about every 7 days, from about every 1 day to about every 14 days, or from about every 1 day to about every 30 days. In various embodiments of the present inventions, the composition is naturally extruded from the subject at the end of treatment via natural processes similar to extrusion of ear wax. In certain embodiments, the composition may naturally break down, and its degradation products may be eliminated by the subject.

A dose is determined based on the minimum inhibitory concentration needed at the site of infection. Without being bound to a particular theory, in various aspects the minimum inhibitory concentration for *H. influenza* or *S. pneumoniae* middle ear infections is about 4 µg/mL for ciprofloxacin. In various aspects, a typical dose will require approximately 12 µg of ciprofloxacin, based on an average middle ear volume of 3 mL. In various embodiments, the compositions will comprise sufficient dose to delivery 12 µg of ciprofloxacin to the middle ear. In various aspects, the administration of the composition comprises a single application. In other aspects, the administration of the composition comprises multiple applications. For example, the composition may be administered two, three, four, or more times. In certain embodiments, the composition is administered repeatedly until the desired clinical outcome is achieved. For example, the infection is resolved.

Kits

In various embodiments the claimed invention further comprises kits, which may additionally comprise the compositions in sterile packaging. The kits may comprise two containers for two-part, matrix-forming agents. The therapeutic agent may be included in one or both of the containers of the matrix-forming agent, or the therapeutic agent may be packaged separately. In various aspects the kits may comprise a bottle or bottles, and a dropper for each bottle. In various aspects, the kits may comprise instructions and prescribing information for administering the compositions contained therein.

EXAMPLES

Example 1

Effects of Chemical Penetration Enhancers on the Permeability of the Chinchilla Tympanic Membrane Localized drug delivery to the middle ear has been limited to invasive perforation of the tympanic membrane ("TM") because of the TM's impermeability to most small molecules. The lateral surface of the TM is a stratified, squamous, keratinizing epithelium that is continuous with that of the external ear canal, and comprises the outermost of the TM's trilayer structure; its composition is identical to that of the epidermis and stratum corneum found elsewhere on the body's surface, except that it consists of 3-5 corneocyte layers rather than the 15-20 layers that cover the rest of the body. The medial, inner-most layer of the TM is also cellular, but consists of a single layer of low cuboidal epithelial cells. The middle layer between the epithelia comprises a complex arrangement of fibroelastic connective fibers, nerve endings, and vasculature [4]. Though fewer than 10 cell-layers and only 50-100 µm thick, the TM is virtually impermeable to all but the smallest, moderately hydrophobic molecules because of the lipidcorneocyte matrix of its outer layer.

Previous observation of the TM's impermeability, and its similarities in nature to that of the skin, has led to experimental adoption of transdermal iontophoresis for local anesthetic administration to the TM prior to myringotomy [7]. However, though chemical penetration enhancers ("CPEs") predate iontophoresis in the transdermal literature, and would appear to be clinically more manageable and cost-effective than iontophoresis apparatus, there is no published evidence of attempts to increase small molecule flux across the TM with CPEs. This is likely due to the lack of verified delivery vehicles approved for clinical use, and the absence of an established in vitro model for measuring TM permeability. The inventions described herein addresses of latter of these barriers by demonstrating effective use of an in vitro model for small molecule trans-TM flux measurement, and provides the first evidence of increased TM permeability to antibiotics using surfactant, terpene, and amino amide CPEs. The relationship between TM permeability and resistivity is further investigated in order to facilitate continued use of this model for development of improved treatments of middle ear disease.

Chemical Enhancers & Formulation Preparation

All compounds were obtained from Sigma (St. Louis, Mo.), unless otherwise specified.

Skin Preparation

Fresh frozen, full-thickness, human abdominal skin (hairless) was obtained from the National Disease Research Interchange (NDRI, Philadelphia, Pa.), and kept at −80° C. for up to 4 weeks before thaw and use. On experiment day 0, full-thickness skin samples were covered with aluminum foil and air-thawed at room temperature. Skin samples were then placed face (stratum corneum) down in a water bath maintained at 60° C. for 2 minutes. Forceps and weighing spatula were then used to separate the epidermis with stratum corneum from the underlying dermis. The dermis was discarded, and any remaining epidermis that was not immediately used for the present experiment was stored in a humidified chamber at 4° C. for up to one week.

Tympanic Membrane Harvesting

Chinchillas were sacrificed by IP administration of a lethal dose of Nembutal, and decapitated to facilitate access to ventral and dorsal regions of the skull adjacent to the temporal bone. In some cases, disjointed heads were frozen, and later thawed in normal (0.9%) saline, before further dissection. Soft tissue of the external ear and surrounding temporal bone was removed by scissors and rongeurs to expose the temporal bone, external auditory meatus (EAM), and auditory bulla, bilaterally. The bullae were carefully opened with a scalpel blade, and the opening enlarged with small rongeurs until the interior-medial surface of the tympanic membrane (TM) and ossicles could be seen. A myringotomy knife was introduced into this opening to sever the malleus-incus ligament, thereby freeing the TM from the surrounding middle ear. The remaining bone surrounding the EAM, lateral to the tympanic ring, was carefully removed until the EAM, tympanic ring, and TM could be separated from the adjacent skull. The removed sample therefore consisted of an intact TM within the tympanic ring, exposed on both lateral and medial surfaces.

Skin Permeability Measurements

Heat-stripped epidermis with stratum corneum (HES) samples were secured between the adjoining orifices of both side-by-side (SxS) and vertical (Franz) diffusion cells (Permegear, Bethlehem, Pa.) with vacuum grease. The receiving chambers for all cells were filled with 3.5 or 5 mL PBS. The donor chamber volumes were 3.5 or 5 mL for the SxS cells and 100 or 200 µL for the Franz cells. At fixed time points (0.5, 2, 6, 24, 48, 120 hours), a 300 µl, sample volume was removed from the receiving chamber and prepared for HPLC analysis of permeant concentration; an equivalent volume of PBS was returned to the receiving chamber.

TM Permeability Measurements

Each extracted TM (including the surrounding tympanic ring and adjacent EAM) was placed upright in a 12-well plate, with the TM surface perpendicular to the well base and the EAM longitudinal axis parallel to the well walls. A 3 mL volume of PBS was added to the well, so that the entire medial surface of the TM was submerged, and 100 µL of PBS, test solution, or gel formulation was pipetted into the EAM to cover the lateral TM surface. At pre-determined time points (0.5, 2, 6, 24, and 48 hours post treatment administration), a 100 µL sample from the 3-mL "receiving chamber" was removed, filtered, and transferred to an HPLC vial.

Discussion

This example provides demonstration of analogous permeability changes in chinchilla TMs and HES in response to individual CPEs, but suggests differences in possible synergies of bupivacaine-limonene, bupivacaine-SLS, and bupivacaine-limonene-SLS combinations for increasing TM permeability to ciprofloxacin. Strong evidence is provided that the difference in stratum corneum thickness between the two membranes influences the relative effects of bupivacaine on SLS and limonene (FIG. 2). This raises questions regarding the transferability or interchangeability between from the transdermal literature to continued TM permeability studies.

When trans-TM ciprofloxacin flux within CPE groups (none v. 1% SLS v. 2% limonene) is compared to the magnitude of their respective effects on TM resistance reduction, there is early evidence of a similar relationship to that reported in skin (FIG. 5).

Here, the log factor by which ciprofloxacin flux, J, is increased over the baseline ciprofloxacin flux (with no CPE), Jf/Ji, is plotted against the log factor of resistance decrease, Ri/Rf. Of interest here is that certain CPE combinations had a greater effect on membrane resistance than on ciprofloxacin flux. The addition of 0.5% bupivacaine to 1% SLS, for example, resulted in an insignificant increase in ciprofloxacin flux compared to 1% SLS alone, yet had a large impact on membrane resistance. This is perhaps due to CPE effects on ciprofloxacin solubility within the donor mixture. When only single CPEs are considered (i.e., 0.5% bupivacaine, 1% SLS, and 2% limonene), there is early evidence of correlation between CPE-induced flux increase and resistance decreased ($R^2$=0.97).

Example 2

In Situ Hydrogel Formulations and their Use in Trans-Tympanic Membrane Drug Delivery Localized, sustained drug delivery for treatment of otitis media (OM) can increase antibiotic efficacy and improve patient compliance, which together reduce the selective pressures responsible for antibiotic resistance generation. Increased permeability of the tympanic membrane (TM) to ciprofloxacin can be achieved using mixtures of various classes of chemical penetration enhancers (CPEs) individually, or in combination to minimize toxicity.

In situ gelation can be achieved by physical or chemical cross-linking using a number of mechanisms. Sensitivity to pH, light, temperature, and force can each provide the mechanism for controlled gelation, the choice of which depends on the site of application, the desired gelation kinetics, and the intended release kinetics of the incorporated therapies. Therapy administered to the external auditory meatus (EAM) for treatment of OM benefits from a rapid liquid-gel transition, so that prolonged restraint or general anesthesia can be avoided in treating children.

P407 is a block copolymer (MW=9,840-14,600) that consists of ethylene oxide (EO) and propylene oxide (PO) blocks arranged in a triblock structure $EQ_x$-$PO_yEO_x$, x=95-105 and y=54-60 [9]. It is a surfactant, with a hydrophilic-lipophilic balance (HLB) of 22 at 22° C., which improves solubility of and stratum corneum permeability to hydrophobic small molecules [10, 11]. However, its property most relevant to in situ-forming delivery systems is its thermoreversible gelation, which allows for easy application of a liquid drop into the external auditory meatus (EAM) and rapid gelation upon contact with the TM (35-37° C.). Chitosan (Ch) and chondroitin sulfate (CS) are oppositely charged polyionic polysaccharides that can gel via polyelectrolyte complexing when properly mixed [12], thereby providing another means of in situ gelation with biocompatible, bioresorbable polymers. These in situ gelling mechanisms are selected because of their simplicity, low cost, and ease of use. The specific polymers are selected because of their previously demonstrated biocompatibility [13-15].

Materials & Methods

Animal Care

All animals were cared for in accordance with protocols approved institutionally and nationally.

Chemical Enhancers and Formulation Preparation

All compounds were obtained from Sigma (St. Louis, Mo.), unless otherwise specified. Hydrogels were prepared as mixtures of gelling polymer (Poloxamer 407 (P407), chitosan (Ch), or chondroitin sulfate (CS)) and CPE (sodium lauryl sulfate (SLS), limonene, and/or bupivacaine) in antibiotic solution (1% ciprofloxacin). Antibiotic/CPE solutions were prepared separately and added to gelling polymers individually. P407 solutions at 18% (w/v) were prepared and allowed to mix overnight at 4° C.; all other polymer solutions or suspensions were prepared at room temperature and set to mix on a stir plate overnight. All mixtures were applied in vitro and in vivo with 1-mL tuberculin syringes capped with a 20-gauge (1.1×48 mm) angiocatheter. Ch and CS polymers for the polyelectrolyte complexes were prepared individually and co-injected with a double-barreled syringe through a single 20-gauge angiocatheter-capped Y-piece.

Skin Preparation

Fresh frozen, full-thickness, human abdominal skin (hairless) was obtained from the National Disease Research Interchange (NDRI, Philadelphia, Pa.), and kept at −80° C. for up to 4 weeks. On experiment day 0, full-thickness skin samples were covered with aluminum foil and air thawed at room temperature. Skin samples were then placed face (stratum corneum) down in a water bath maintained at 60° C. for 2 minutes. Forceps and weighing spatula were then used to separate the epidermis with stratum corneum from the underlying dermis. The dermis was discarded, and any remaining epidermis that was not immediately used for the present experiment was stored in a humidified chamber at 4° C. for up to one week.

Tympanic Membrane Harvesting

Chinchillas were sacrificed by IP administration of Nembutal, and decapitated to facilitate access to ventral and dorsal regions of the skull adjacent to the temporal bone. In some cases, disjointed heads were frozen, and later thawed in normal (0.9%) saline, before further dissection. Soft tissue of the external ear and surrounding temporal bone was removed by scissors and rongeurs to expose the temporal bone, external auditory meatus (EAM), and auditory bulla, bilaterally. The bullae were carefully opened with a scalpel blade, and the opening enlarged with small rongeurs until the interior-medial surface of the tympanic membrane (TM) and ossicles could be seen. A myringotomy knife was introduced into this opening to sever the malleus-incus ligament, thereby freeing the TM from the surrounding middle ear. The remaining bone surrounding the EAM, lateral to the tympanic ring, was carefully removed until the EAM, tympanic ring, and TM could be separated from the temporal bone. The removed sample therefore consisted of an intact TM within the tympanic ring, exposed on both lateral and medial surfaces.

Skin Permeability Measurements

Heat-stripped epidermis with stratum corneum samples were secured between the adjoining orifices of both side-by-side (SxS) and vertical (Franz) diffusion cells (Permegear, Bethlehem, Pa.) with vacuum grease. The receiving chambers for all cells were filled with 3.5 or 5 mL PBS. The donor chamber volumes were 3.5 or 5 mL for the SxS cells and 100 or 200 µL for the Franz cells. At fixed time points (0.5, 2, 6, 24, 48, 120 hours), a 300 µL sample volume was removed from the receiving chamber and prepared for HPLC analysis of permeant concentration; an equivalent volume of PBS was returned to the receiving chamber.

TM Permeability Measurements

Each extracted TM (including the surrounding tympanic ring and adjacent EAM) was placed upright in a 12-well plate, with the TM surface perpendicular to the well base and the EAM longitudinal axis parallel to the well walls. A 3 mL volume of PBS was added to the well, so that the entire medial surface of the TM was submerged, and 100 µL of PBS, test solution, or gel formulation was pipetted into the EAM to cover the lateral TM surface. At pre-determined time points (0.5, 2, 6, 24, and 48 hours post treatment administration), a 100-µL sample from the 3-mL "receiving chamber" was removed, filtered, and transferred to an HPLC vial.

Skin and TM Electrical Impedance Measurements

The electrical impedance of the skin was measured as previously described (Tang et al., 2001). Ag—Cl electrodes (In Vivo Metrics, Healdsburg, Calif.) were placed on either side of the biological membrane (human epidermis with stratum corneum or chinchilla TM), in the donor and receiving media, and a signal generator (Hewlett Packard, HP 33120A) provided a 100 mV AC voltage for 5-10 seconds. The current passing through the membrane was measured with a Fluke Multimeter (Model 139, Fluke Corporation), and the electrical impedance was obtained using Ohm's Law. Background impedance measurements of PBS alone were made separately and subtracted from the initial impedance calculation to yield the membrane impedance; following the final time point in the extracted TM experiments, the TM surface was covered with a thin rubber disc and silicone adhesive, and the electrical impedance of the surrounding tympanic ring and EAM were measured and similarly subtracted from the initial TM+EAM impedance calculation. Any skin sample with an initial impedance x exposed area value of <50 kOhm*cm$^2$ was considered damaged, was discarded, and was subsequently replaced with an intact sample (Kushner et al., 2004; Kasting & Bowman, 1990).

High Performance Liquid Chromatography (HPLC)

Samples from each time point were filtered with 0.2 µm syringe filters (Acrodisc, Sigma) and pipetted into 100-µL HPLC vial inserts. Assays were performed on a Hewlett-Packard HP 1100 HPLC system. Samples in 20-µL volumes were injected onto a 4.6 (ID)×250 (L) mm Atlantis dC$_{18}$ 5 µM column. The column was eluted with an aqueous solution of 80:20 acetonitrile:NaH$_2$PO$_4$/H$_3$PO$_4$ (0.01M, pH=2.8) at 1 mL/min. Ciprofloxacin was detected by UV absorbance at 275 nm wavelength. Separate dilution standards were prepared by diluting 1% Ciprofloxacin solution (Bayer HealthCare, West Haven, Conn.) in PBS, 0.01% to 1.0×10$^{-5}$% (w/v), on the day of analysis.

Chinchilla middle ear fluid (MEF) and plasma samples were prepared as previously described [16]. A 50-µL sample of MEF, plasma, or standard was added to 2 mL acetonitrile and 20 µL of 10 µg/mL levofloxacin (internal standard), vortexed, and centrifuged at 1500 g for 10 minutes. The 2 mL acetonitrile was then syringe-filtered into transferred to a 10×75 mm culture tube and evaporated at 50° C. under nitrogen. The residue was constituted in 100 µL mobile phase and transferred to 100-µL HPLC vials inserts for analysis.

Hydrogel Mechanics & Formulation Assessment

Gelation times were measured in HPLC vials (10×25 mm) suspended in a 35° C. water bath over a heated stir plate set to 200 rpm. After allowing for the vial temperature to equilibrate with that of the surrounding water, 0.1-1 mL of each gel was injected into a vial with an angiocatheter-capped 1-mL syringe. The gelation time was defined as the time required for the stir bar to stop rotating.

Release kinetics of ciprofloxacin from hydrogels was assessed in 12-well plates with transwell inserts. Transwell inserts (0.2 µm filter) were inserted into wells filled with 3 mL PBS. Equal volumes of gels were applied to the inserts, and 0.1 mL volumes of the PBS receiving medium were sampled at fixed time points (0.25, 0.5, 1, 2, 6, 24, 48 hrs) and replaced with an equal volume of PBS. Samples were chromatographically analyzed with HPLC for determination of ciprofloxacin concentrations.

Rheological data was collected with an ARG-2 controlled stress rheometer (TA Instruments). A 40 mm parallel plate was used with gap distances between 0.3 and 0.6 mm with 0.7 mL of hydrogel, depending on the formulation. Adhesive-backed 600-grit silicon carbide sandpaper was placed on the sample platform and oscillating plate in order to minimize slippage between the hydrogel formulations and the shearing surface. Oscillatory stress sweep experiments were conducted with systematic ramping of stress amplitude from 0.5 to 200 Pa at 3 radians/sec oscillation frequency to identify the linear viscoelastic range. Frequency sweeps were conducted between 0.1 and 500 radians/sec at the stress value corresponding to the linear viscoelastic region of the oscillatory stress sweep output (typically between 10 and 40 Pa); these allowed for evaluation of elastic and loss moduli of the materials as a function of applied shear. Steady shear rate sweeps between 0.05 and 200 $s^{-1}$ were applied to measure the shear thinning behavior of the polyelectrolyte gels.

Chinchilla Model of Otitis Media

Adult male chinchillas (400-600 g) were anesthetized with Ketamine (30 mg/kg) and Xylazine (4 mg/kg) and initially evaluated by tympanometry and otomicroscopy to confirm normal middle ear status. The fur covering the superior bullae was removed bilaterally, the bullae opened 3-5 mm with a scalpel, and 25 CFU non-typable *Haemophilus influenzae* (NTHi) in 100 μL Hanks balanced solution was inoculated directly into the middle ear, bilaterally, via the bullae openings. At 48 hours post-inoculation, tympanometry and otoscopy were again used to assess presence of TM inflammation, negative middle ear pressure, and/or middle ear effusion. Nasopharynx (NP) lavage was performed and cultured evidence of bacteria, and the bullae openings are re-opened for middle ear analysis. The contents of the middle ear were examined through an operating microscope, and mucosa samples collected for direct culture with a calcium alginate swab and streaked on chocolate agar plates. Middle ear fluid (MEF) was collected with an angiocatheter-capped 1-mL syringe; 500 μL Hanks balanced solution was used for lavage of middle ear cavities if MEF was not present. Approximately 1.5 mL blood was obtained by superior sagital sinus puncture on day 2 post-inoculation, but before application of antibiotic treatment; samples were also drawn on day 7 post-inoculation (day 5 post-treatment).

Following tympanometric, otoscopic, and bacteriologic assessment of otitis media (OM) status on day 2, 500 μL hydrogel formulation was applied to the external autidory meatus (EAM) using a speculum and guided by a surgical microscope. Left ears were always treated with the test formulation, which consisted of antibiotic, gel polymers, and chemical penetration enhancers (CPEs). Right ears were used as controls; no-treatment controls, drug-gel controls (no CPEs), and gel-only controls (no CPEs, no drug) were all used. Middle ear and nasopharyngeal samples were collected on days 4 (post-treatment day 2), 7 (post-treatment day 5), and 11 (post-treatment day 9) and cultured to quantify CFUs.

Tissue Harvesting & Histology

Chinchillas were deeply anesthetized by IP administration of ketamine and Nembutal at twice the normal dosage. Middle ears were extracted as described above, quickly rinsed with PBS, and immediately soaked in Accustain (non-formalin fixative). Samples were kept in fixative at room temperature for one week, then transferred to 10% ethylene diamine tetraacetic acid (EDTA) to decalcify bone of the external auditory meatus (EAM), tympanic ring, and middle ear. After two weeks, the decalcified bone of the bulla was removed, leaving only the EAM, tympanic ring with intact TM, and the lateral wall of the middle ear cavity. Samples were then embedded in paraffin, sectioned (5 μm thick) to yield three cross-sections of the TM along the axis of the EAM, and stained with hematoxylin and eosin.

Auditory Brainstem Response (ABR) Measurements

ABR experiments were conducted with a custom-designed stimulus generation and measurement system built around National Instruments (Austin, Tex.) software (Lab View) and hardware. The hardware included a GPIB controller and an ADC board. The custom LabView program computed the stimuli, and downloaded the stimuli to a programmable stimulus generator (Hewlett Packard 33120A). The stimulus was then filtered by an antialiasing filter (KrohnHite 3901) and attenuated (Tucker-Davis Technologies). The filter and the attenuator were controlled by the LabView software. Simultaneous with stimulus output, the 2 ADC channels sampled the amplified ABR signal and the output of a microphone sealed in the ear canal of the animal.

The acoustic stimuli were pairs of 20-ms tone bursts of opposite polarity. The frequency of the bursts increased from 500 Hz to 16 kHz in octave steps. Each burst was sine windowed, with 40 ms between the two bursts. ABR responses to 250 pairs of stimuli were averaged at each stimulus level. The ABR response was computed from the sum of the averaged response to the two different polarities. Stimulus level was varied in 10 dB steps. A visual judgment of threshold at each stimulus frequency was determined post-measurement in a blinded fashion.

The attenuated stimulus was played through a hearing-aid earphone placed within the intact ear canal of adult female chinchillas (400-600 g) anesthetized by IP administration of Ketamine and Nembutal (50 mg/kg). The earphone coupler included a microphone that monitored the sound stimulus level. ABRs, obtained in a sound-attenuating booth, were measured with a differential amplifier with a gain of 10,000 and a measurement bandwidth of 100 Hz to 3 kHz. The measurements were obtained from the positive electrode in the muscle behind the measured ear; the negative electrode was at the cranial vertex, and the ground electrode behind the contralateral ear.

Statistical Analysis

Data that were not normally distributed are presented as medians with $25^{th}$ and $75^{th}$ percentiles and compared by Mann-Whitney U-test. Normally distributed data, such as MTT assay results, are described parametrically with means+/−standard deviations and compared by t-tests and analysis of variance (ANOVA). Statistical significance, for both parametric and nonparametric tests, was defined as $P<0.05$.

P407 Formulations and Release Kinetics

Figure 11:
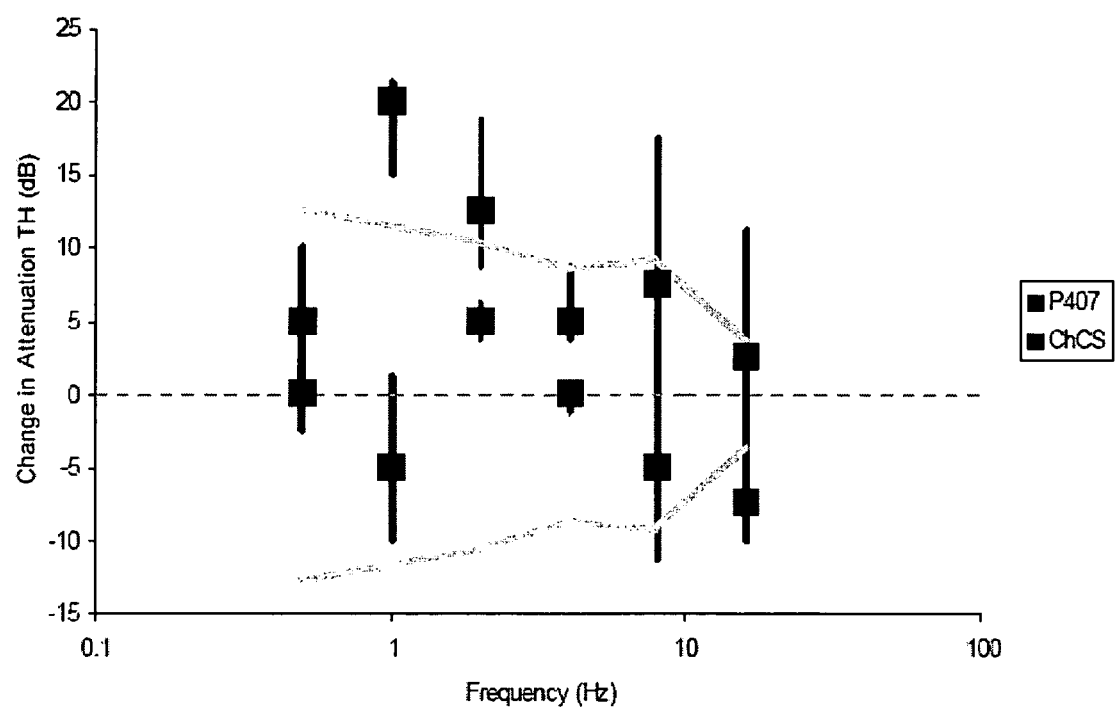
Figure 12:
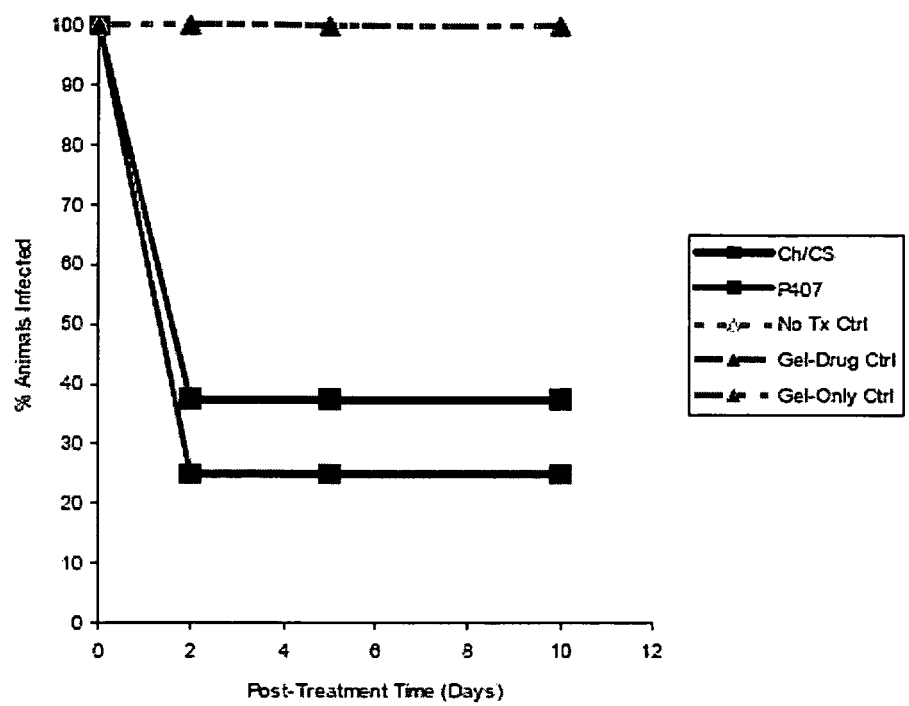

P407 in 1% ciprofloxacin solution has a shifted gelation temperature ($T_{gel}$)-concentration curve compared with that of P407 prepared in water (FIG. 11). This is consistent with P407's behavior in other solvents [17-19], suggesting that the dependence of micelle formation on temperature is altered, but not fundamentally inhibited by the ciprofloxacin or its low pH of 3-4. The P407 concentration identified as that which gels at 35° C. is 18% (w/v) in 1% ciprofloxacin solution, with or without 0.5% bupivacaine+1% SLS or 0.5% bupivacaine+2% limonene. The time required for these P407 mixtures to gel at 35° C., from 22° C., was less than 10 seconds, and increased slightly with increased volume, from 0.1 to 1 mL, when applied to a geometry similar to that of the EAM (FIG. 12).

Figure 13:
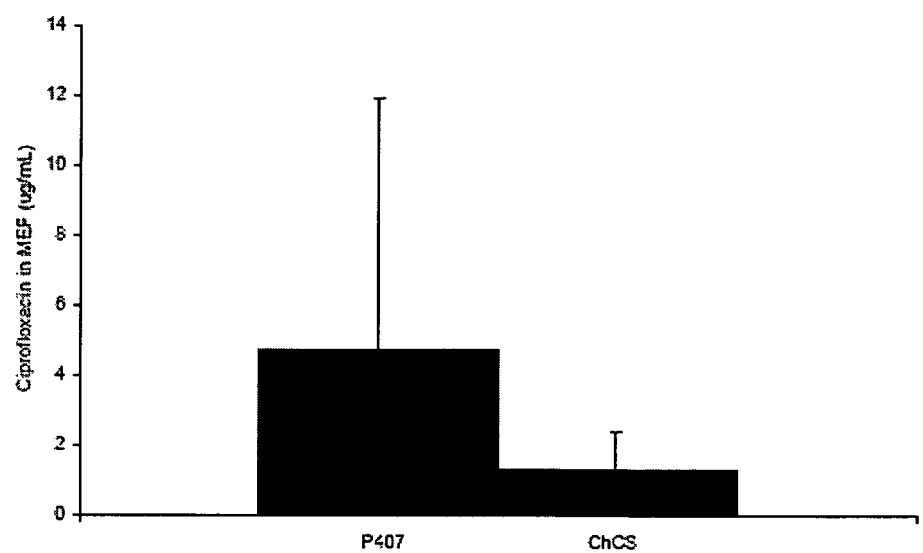
Figure 14:

Though ciprofloxacin (MW=331.346) is small enough that it should be minimally effected by the micelle or cross-linked networks of polymer gels, the formulation environment can change the solubility of ciprofloxacin, and thereby alter its release kinetics. To investigate the effects of adding gelling polymers and CPEs to the ciprofloxacin solution, release of ciprofloxacin from P407 into PBS was compared between gels with and without CPEs (FIG. 13).

Release kinetics from 18% P407 both with and without CPEs demonstrate sustained release into an aqueous receiving medium. Though these release percentages do not necessarily correlate with release into or across the stratum corneum of the TM, they suggest a decrease in free ciprofloxacin with the addition of 0.5% BPV and 1% SLS.

Chitosan-Chondroitin Sulfate Formulations and Release Kinetics

Figure 20:
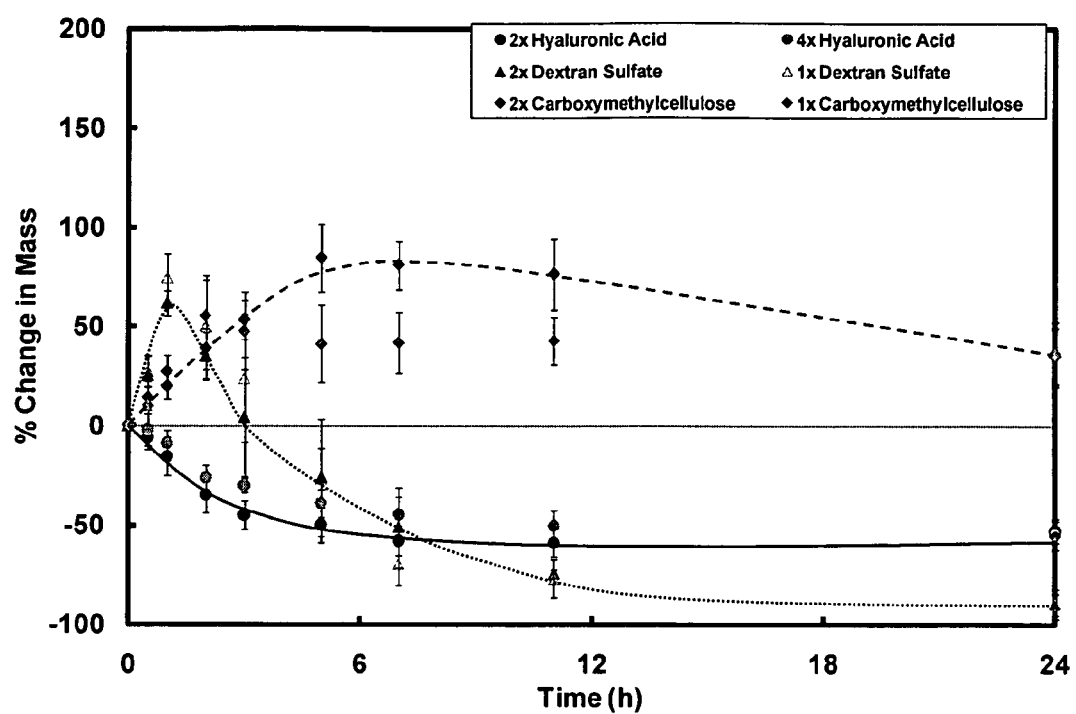

A 1:1 mixture of 12% chitosan (Ch) and 12% chondroitin sulfate (CS) in 1% ciprofloxacin solution was found to gel through polyelectrolyte complexing when extruded through a 20-gauge angiocatheter-capped double-barreled syringe. Gelation was dependent on initial separation of the polycationic chitosan and polyanionic chondroitin sulfate, as well as on the diameter of the extruding vessel; pre-mixture of the two polymers appeared to inhibit complex formation, as did lower-gauge needles or angiocatheters. The gelation time of the Ch/CS polyelectrolyte complex was more difficult to quantify; though complex formation increased viscosity enough to keep between 0.1 and 1 mL of gel at the bottom of an inverted vial indefinitely, the gel consistency was such that stir bar rotation was never impeded. Still, Ch/CS complexes sufficiently gelled in less than 30 seconds and were not sensitive to temperature (22-35° C.), nor to the presence of CPEs.

Ciprofloxacin release from Ch/CS gels into an aqueous receiving medium did not significantly differ between formulations with and without CPEs (FIG. 14), but the release rate of both was intermediate between those of P407±CPEs.

Ciprofloxacin Flux Across the Tympanic Membrane v. Condition in Gel

Ciprofloxacin release from P407 and Ch/CS hydrogels across the TM is expected to be different from those measured from gels into an aqueous solution. Release into an aqueous medium is dominated by concentration differences between the gel and the receiving medium. the porosity and tortuosity of the gel, and the relative size of the molecule(s) being released. Trans-TM penetration of the same molecule(s), however, is additionally influenced by the gel-TM partition coefficient, the diffusivity of the TM, and the TM-receiving medium partition coefficient. In vitro trans-TM flux of ciprofloxacin from P407 and Ch/CS hydrogel carriers is also different from that observed from otherwise identical CPE-ciprofloxacin mixtures in solution, in the absence of gelling polymers (FIG. 15). The effect of hydrogel polymers on ciprofloxacin release across the TM is similar to that seen on release into an aqueous medium: the reservoir environment results in decreased ciprofloxacin solubility, and therefore a decrease in steady-state flux.

However, the time lag to reach this steady-state is decreased with the addition of the gels, resulting in decreased time required to exceed the minimum inhibitory concentration (MIC) for eradication of resistant *H. influenzae* and *S. pneumoniae.*

Auditory Brainstem Response (ABR)

ABR measurements provide noninvasive assessment of hearing sensitivity by collecting multiple averages of compound action potentials in response to acoustic stimuli. Baseline measurements, before application of gels, reveal increasing sensitivity (decreased thresholds) from 500-Hz to 4-kHz tones, and a subsequent increase in thresholds from 4 to 16 kHz. The applied P407 solution was able to form a thin, near-uniform layer, covering all or most of the TM surface before gelling; the Ch/CS gel, however, took the form of an adherent, viscous bolus, typically in the middle of the TM inferior to the umbo. Ch/CS resulted in small threshold increases immediately after application, but P407 had no significant effect on hearing sensitivity (FIG. 16). The Ch/CS-induced threshold increases were observed across all frequencies, but appeared to be significant only at 1 kHz based on the distribution of the pre-application measurements across all animals.

Subsequent ABR measurements were made 2 and 10 days after gel application for evidence of harmful effects to the TM that might result from prolonged exposure to the CPEs. The median change in thresholds among individual animals at days 0, 2, and 10 revealed no systematic trend or significant differences in threshold shift as a function of time. Though some individual thresholds changed from the immediate (day 0) post-application measurement to the day 10 measurement, there were no significant changes found within the two populations (i.e., P407 and Ch/CS) between day 0 and day 10.

OM Eradication

Though sufficient ciprofloxacin flux across the TM is achieved in vitro by simple mixtures of P407 or Ch/CS with CPEs, structural and physiological changes in the TM during active disease [20] may alter the kinetics of ciprofloxacin permeating the TM and entering the middle ear fluid (MEF) and middle ear mucosa. The efficacy of P407 and Ch/CS mixtures was therefore investigated in an in vivo model of OM. Compared to no-treatment controls, gel-drug controls (no CPEs), and gel-only controls (no ciprofloxacin or CPEs), both P407 and Ch/CS mixtures were effective at eradicating *H. influenzae* infection (FIG. 17). Though the majority of animals in each treated group experienced complete eradication of bacteria within 48 hours of treatment, a small minority of animals in each group remained with non-0 CFU counts (1 of 4 in the P407 group; 3 of 8 in the Ch/CS group).

To investigate the possibility that incomplete eradication of disease in all animals was due to insufficient ciprofloxacin levels reaching the middle ear, MEF samples were analyzed to determine levels of ciprofloxacin at 48 hours post-treatment (FIG. 18). Animals in which infection was eradicated (0 CFU at 48 hours) consistently had MEF ciprofloxacin concentrations greater than 1 μg/mL and as high as 19 μg/mL; those animals with remaining infection were found to have less than 0.5 μg/mL MEF ciprofloxacin concentrations.

Plasma samples were also analyzed for evidence of systemic ciprofloxacin delivery via TM vasculature. Though significant sink effect was not anticipated based on estimates of the metabolic activity of the TM and skin of the EAM [21], it is possible that OM-induced inflammation and associated increases in blood flow might result in significant systemic absorption. Plasma samples collected from the superior sagital sinus at 2 and 5 days post-treatment contained no detectable ciprofloxacin (detection limit approximately 100 ng/mL; 97±2% recovery from spiked control plasma samples).

Toxicity

Continued investigation of acceptable topical formulations for trans-TM drug delivery in general or OM treatment in particular is dependent on in vivo demonstration of safety. Though the individual components of the mixtures used here are minimally toxic in keratinocyte and fibroblast in vitro assays [8], the in vivo effects of prolonged exposure to the TM have not been studied. P407 and Ch/CS mixtures, including ciprofloxacin and CPEs, were exposed to TMs in vivo in normal and *H. influenzae*-infected chinchillas for 7-10 days. Histopathology of TMs was compared at stereotyped cross-sections (FIG. 19) for evidence of changes in inflammatory indicators, such as polymorphonucleocyte (PMN) and granulocyte infiltration, blood vessel dilation, or edema.

Sections of normal TM (FIG. 20, A) were consistently 15-20 μm thin, with a clearly visible stratum corneum and a dominant fibrous middle layer. Normal TMs treated with Ch/CS or P407 mixtures (FIG. 20, B and C, respectively) showed signs of minor toxicity, primarily in a slight thickening of the TM due to an apparent reactive hyperplasia in the stratified, squamous epithelium; though generally very similar, TMs treated with the P407 mixture were consistently slightly thicker than those exposed to the Ch/CS treatment. TMs extracted after 11 days of untreated *H. influenzae* middle ear infection (FIG. 20, D) were 5-10 times thicker than normal TMs due to edema and hyperplasia in both lateral and medial layers on either side of the fibrous middle layer. However, when the same infections were treated with a single application of either P407 or Ch/CS mixture, TMs were found to return to near-normal thickness by day 7-post treatment (FIG. 20, E).

Discussion

Figure 17:
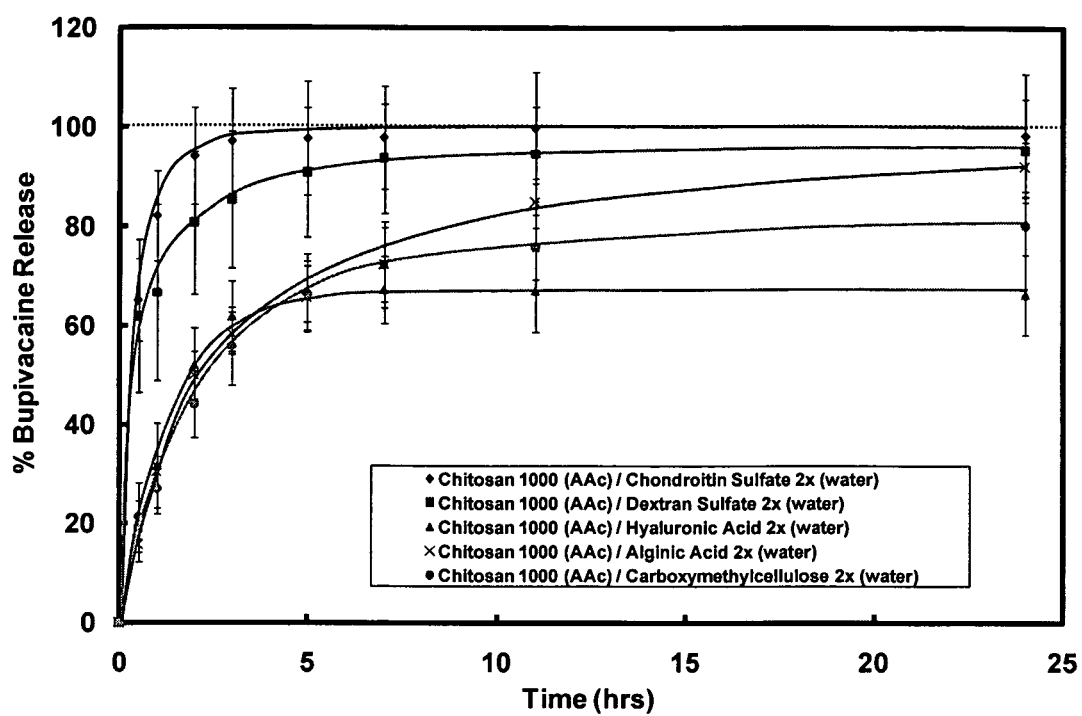

Despite a decrease in ciprofloxacin release from the P407 gel system with the introduction of CPEs (FIG. 13), the P407/CPE treatment was at least as effective as the Ch/CS/CPE system at eradicating *H. influenzae* in an animal model of OM (FIG. 17). To maximize the efficacy of either treatment, however, it is important to understand the reservoir environment so that the concentration of free ciprofloxacin is maximized within the given carrier. P407/ciprofloxacin solutions with and without 0.5% bupivacaine+1% SLS remain at similar pH (between 3.2 and 3.5), suggesting the altered release rate is not due to a change in ciprofloxacin solubility resulting from pH increase. More likely, the presence of an additional 10 mg/mL of solute leads to saturation and ciprofloxacin precipitation.

Trans-TM delivery of ciprofloxacin from P407 prepared with 0.5% bupivacaine and 2% limonene, without 1% SLS, was investigated because aqueous ciprofloxacin release was not altered by limonene in the Ch/CS/bupivacaine/limonene mixture. However, poor trans-TM delivery of ciprofloxacin in vitro was found, likely as a result of limonene binding within the hydrophobic domains of the P407 during micelle formation. The in vitro trans-TM ciprofloxacin flux was statistically equivalent for the P407/bupivacaine/SLS and Ch/CS/bupivacaine/limonene mixtures.

Figure 15:
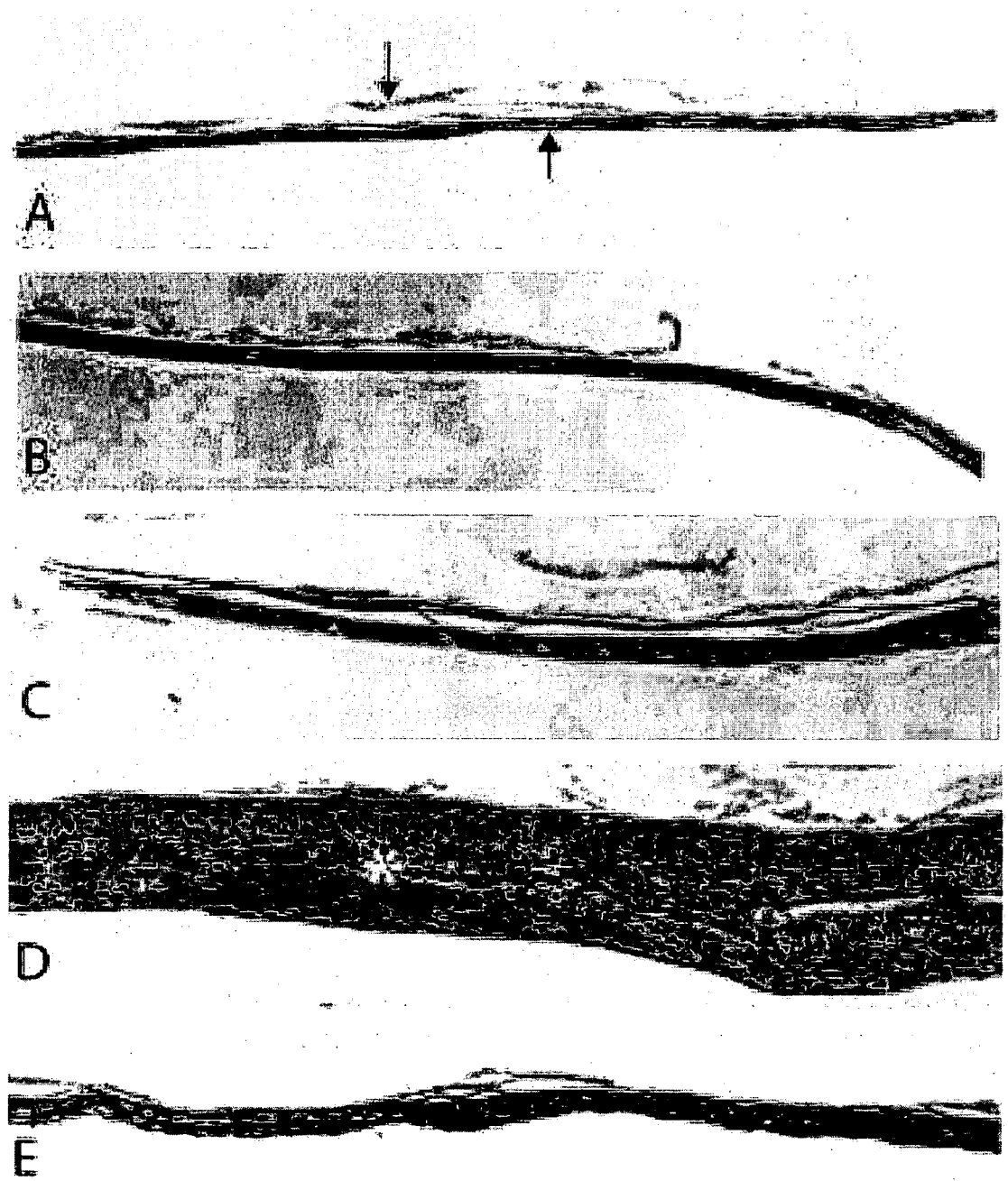

Addition of 2% limonene to P407+bupivacaine+SLS resulted in grossly heterogeneous mixtures with widely variant mechanical/gelation properties. Incorporation of 1% SLS to Ch/CS mixtures, with or without inclusion of bupivacaine and/or limonene, inhibited Ch/CS complex formation, likely because of SLS's anionic interference with the normal polyelectrolyte interactions. The trans-TM ciprofloxacin delivery profiles (FIG. 15) suggest the incorporated CPEs in both P407 and Ch/CS mixtures are sufficiently effective at rapidly increasing stratum corneum permeability, based on the short time required to reach MIC levels.

Figure 16:
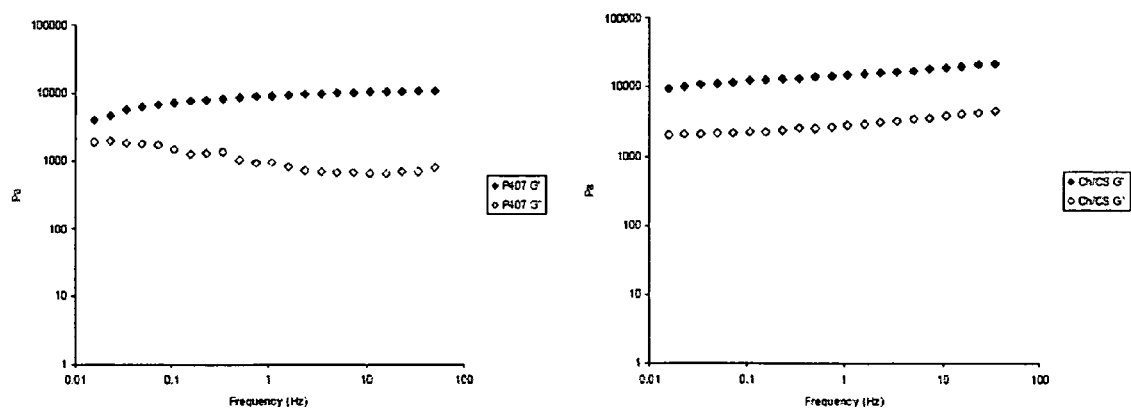

OM commonly increases auditory thresholds because of inflammation, negative middle ear pressure, and/or middle ear fluid (MEF), which alone or in combination change TM admittance, and therefore its conductive properties [22-26]. As hydrogel density is close to 1 g/mL and TM diameter about 8 mm, a 100 µL drop is approximately 100 mg distributed across a 2 mm-thick layer. Given that P407 and Ch/CS mixtures have similar densities, the observed differences in induced auditory threshold shifts (FIG. 16). Preliminary rheological data (FIG. 21) provide storage (G') and loss (G") moduli of P407 and Ch/CS gels that imply a high degree of elasticity in both gels (G'>5,000-10,000 Pa), but different viscosity effects. While Ch/CS demonstrates classic elasticity in the consistent phase angle ($\delta=0.191\pm0.00970$) across frequencies, P407 shows more viscoelastisity ($\delta=0.434$ to $0.067$ with increasing frequency).

Gel application to animals with OM led to median MEF ciprofloxacin levels that appeared to be higher in the P407 group than in the Ch/CS group. Though it is likely true that the Ch/CS group had a lower cure rate because a lower concentration of cipro permeated the TM on average, it is likely that the Ch/CS group had a MEF cipro levels and lower cure rate because the gel did not stay in the ear canal as consistently as in the P407 popultion. This possibility is confirmed by in vitro demonstration that Ch/CS gelation takes longer than P407 gelation. Though Ch/CS mixtures gel quickly (less than 30 s), the animals with remaining infection were noted to be lightly anesthetized during application, and shook their heads immediately upon or shortly after administration.

Example 3

Polyelectrolyte Complexes

Methods: Polyelectrolyte complexes based on chitosan as the cationic component and chondroitin sulfate (CS, low molecular weight), dextran sulfate (DS, low molecular weight), hyaluronic acid (HA, molecular weight 700 kDa), alginic acid (AA, medium molecular weight), or carboxymethyl cellulose (CMC, medium molecular weight) as the anionic component were prepared by dissolving the polymers individually in aqueous solutions and mixing the polymers by co-extruding them through a 25G double barrel syringe. Each polymer was dissolved at 3 wt % unless otherwise noted, with the cationic polymer (chitosan) dissolved in 0.3M acetic acid (AAc), 0.2M hydrochloric acid (HCl), or a pH 4 0.3M citric acid buffer and the anionic polymer dissolved in water or phosphate-buffered saline (PBS). Unless otherwise noted, acetic acid was used as the chitosan solvent and water was used as the anionic polymer solvent. In some cases where specified, solution concentrations of 2× (6 wt %) or 4× (12 wt %) of the base 3 wt % concentration were analyzed. It should be noted that each polyelectrolyte combination tested gelled within 10-30 seconds of extrusion through the double-barrelled syringe. For assaying the drug delivery potential of such blends, 10 mg/mL bupivacaine hydrochloride was dissolved in the cationic polymer solution, resulting in 5 mg/mL bupivacaine in the final polyelectrolyte complex.

Drug delivery and complex swelling was assayed using a Transwell plate technique. 300 mg of each polyelectrolyte complex to be tested was extruded into a basket insert backed with a 0.4 µm membrane. Twenty holes were punched into the membrane using a 25-gauge needle to facilitate free flow of fluid between the cup insert and the surrounding fluid. The basket inserts were then placed in a 12-well plate and 2 mL of phosphate-buffered saline (PBS) was added. The plate was then placed on a shaker platform in a 37° C. oven. At predetermined intervals, the basket inserts were removed from the test well, dried, and weighed. The drug concentration in the test well was assayed by UV/VIS spectrophotometry. A fresh aliquot of 2 mL PBS was then added to a fresh well and the plates were returned to the shaker. Results are expressed as the percentage of bupivacaine release relative to the initial 5 mg/mL bupivacaine concentration in the pre-complex solution and the percentage mass change of the blends, related to both swelling and dissolution of the polymer blend over time. Error bars represent the standard deviation of four replicate runs.

The cytotoxicity of the complexes was evaluated using an MTT with mouse-derived C2C12 myoblasts (cultured in Invitrogen DMEM medium supplemented with 20% fetal bovine serum and 1% penicillin streptomycin) and mouse-derived 3T3 fibroblasts (cultured in ATCC DMEM medium supplemented with 10% calf serum albumin and 1% penicillin streptomycin). Each cell line was plated in 1 mL aliquots in a 24-well plate at a density of 50000 cells/well and permitted to adhere over 24 hours. In the case of the C2C12 myoblasts, the FBS growth medium was replaced with 2% horse serum and 1% penicillin streptomycin-supplemented DMEM media to differentiate the myoblasts into myotubes over the course of 12 days, with regular media changes every 3 days. Passages 3-25 of the cells were used for biocompatibility studies. Materials were sterilized in their dry state under a UV lamp over a period of three hours, after which 0.9% saline solution was added aseptically. Double-barrel syringes were loaded with material using the extrusion method described previously carried out in a sterile environment. Materials were applied to the plated cells using a 25 G syringe in 0.1 mL aliquots. Four replicate wells were tested for each material, with media-only and cell-only controls (also performed in quadruplicate) also included on each 24-well plate tested. At time points of 24 hours and 4 days after material addition, both the media and the test material was removed and replaced with 1 mL of fresh media and 100 μL of MTT reagent. Solubilization solution (Promega) was added after four hours of incubation and the plates were mixed on an orbital stirrer for 24 hours. The absorbances of each of the wells were then measured in duplicate in a 96-well plate using a multi-well plate reader (Molecular Devices) operating at 570 nm. Results are baseline-corrected to eliminate the impact of media absorbance and are normalized relative to the cell-only results.

Figure 18:
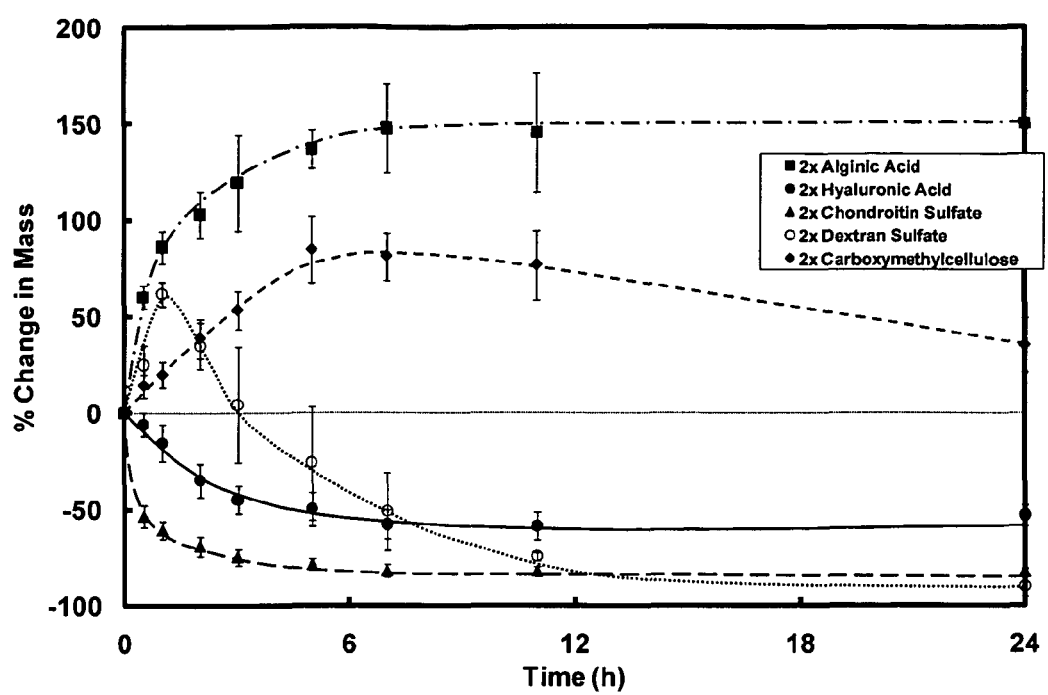

Effect of Anionic Polymer Type: FIG. 17 shows the release kinetics of bupivacaine from polyelectrolyte complexes of high molecular weight chitosan and each of the five anionic polysaccharides tested, mixed at a 1:2 mass ratio. FIG. 18 shows the percentage mass change as a function of time for the same polyelectrolyte complexes analyzed in FIG. 17. In this case, the occurrence of a positive mass change indicates that the polyelectrolyte complex is swelling while a negative mass change indicates that the polyelectrolyte complex is de-swelling relative to its original water content immediately after mixing.

In each case, drug release from the chitosan-anionic polyelectrolyte complexes is dependent on the degree of ionic cross-linking facilitated by each complex mixture, the viscosity of the resulting complex, and the osmotic driving force for complex swelling. The mass change data primarily represents the balance between the ionic cross-linking and osmotic swelling driving forces for drug delivery, while the drug release kinetics also incorporate the effect of the complex viscosity. Complexes based on dextran sulfate or chondroitin sulfate release drug relatively quickly; correspondingly, these complexes rapidly lose mass upon mixing, although the dextran sulfate complex briefly swells before de-swelling. This observation suggests that the interaction between these anionic polymers and chitosan is very strong, causing water (and the dissolved drug) to be rapidly pumped out of the polyelectrolyte complex via an active transport mechanism and accounting for the observed mass loss and the extremely rapid and nearly complete release of bupivacaine observed. In contrast, both alginic acid and carboxymethyl cellulose complexes swell over time upon exposure to phosphate buffered saline, suggesting weaker intermolecular interactions in this case. Correspondingly, while drug release is promoted by the increased water content (i.e., porosity) of the swollen complexes, drug is not actively pumped from complex as it is during the de-swelling of the dextran sulfate and chondroitin sulfate complexes and the overall drug release from the complexes is significantly slower. Hyaluronic acid-chitosan complexes display intermediate behavior in that they deswell over time but do so more slowly and to a lower overall degree than the dextran sulfate or chondroitin sulfate complexes, decreasing in mass by ~50% at steady state compared to ~90% for the dextran sulfate and chondroitin sulfate complexes. As a result, only a portion of the drug is released from the complex from active transport (via water expulsion) and ~35% of the drug remains trapped inside the complex even after long release times given the relatively small porosity of the de-swollen complex. Hence, by choosing the polyelectrolyte used to prepare the complexes, drug release can be accelerated or decelerated based on the strength of the inter-polymer interactions and the resulting swelling response of the complex over time.

Figure 19:
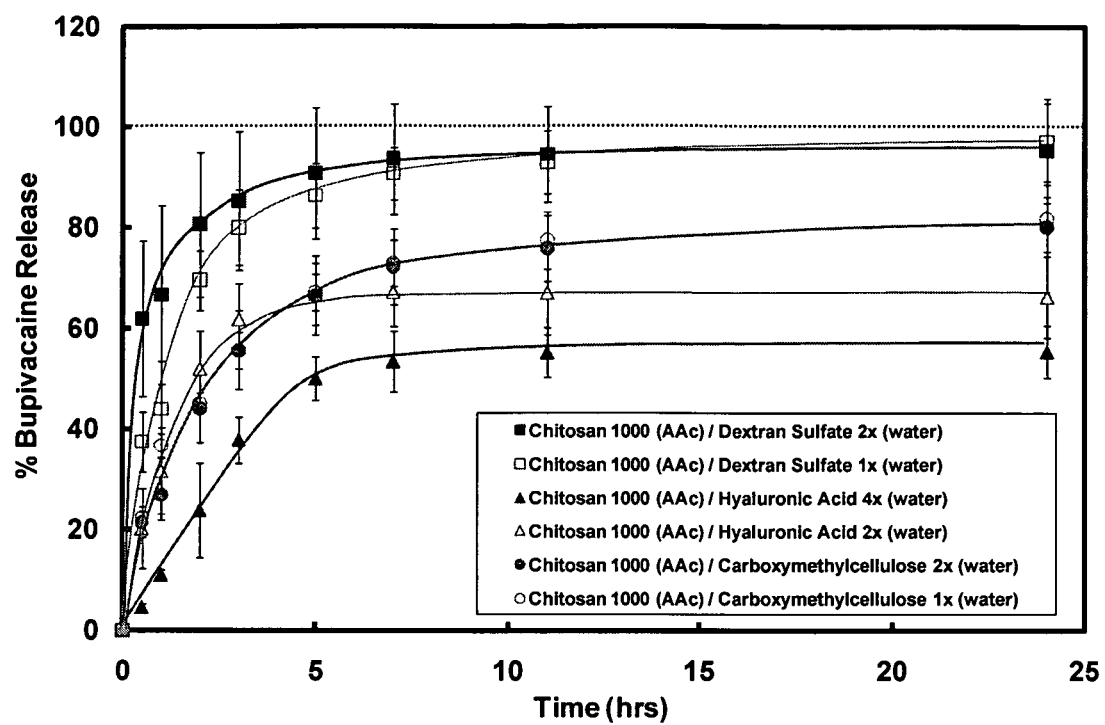

Effect of Polymer Concentration: FIG. 19 compares the drug release kinetics of high molecular weight chitosan-polyanion complexes prepared at different polyanion concentrations, while FIG. 20 compares the percentage mass changes in the complexes as a function of time for each of the complexes tested in FIG. 19.

FIGS. 19 and 20 illustrate the combined effects of changing the swelling response of the complex and changing the polymer chain density (i.e., viscosity) of the complex when the concentration of one or both of the polymer components of the blend is increased. Regardless of the polymer used, the complex viscosity and the osmotic driving force for complex swelling both increase as the polymer concentration in the complex increases. However, depending on the polyanion used, the increased intermolecular interactions (i.e., ionic cross-linking) induced by the higher concentration of polymer in the complex volume may also play an important role in the complex behavior. The balance of these interactions determines the drug release properties of the complex. For complexes with relatively weak intermolecular interactions (carboxymethyl cellulose-chitosan and alginic acid-chitosan), the osmotic driving force for complex swelling increases more than ionic cross-linking when adding additional polymer. Thus, while the higher polymer concentration complex swells more, it is also more viscous; these effects roughly offset each other in this case, resulting in approximately equal drug release for both the 1× (3 wt % CMC solution) and 2× (6 wt % CMC solution). Conversely, for complexes with strong intermolecular interactions (dextran sulfate-chitosan and chondroitin sulfate-chitosan), the increased polymer concentration significantly increases ionic cross-linking within the complex, reducing the water content of the complex throughout the entire de-swelling process and overriding the increased osmotic gradient which would promote complex swelling. This higher degree of de-swelling drives increased active transport of water (and dissolved drug) from the complex, resulting in the faster drug release for the 2× (6 wt % dextran sulfate) complexes compared to the 1× (3 wt % dextran sulfate) complexes. Hyaluronic acid-chitosan complexes display intermediate behavior, with the 4× (12 wt % hyaluronic acid) complexes de-swelling slightly less over time than the 2× (6 wt % hyaluronic acid) complexes. Accordingly, based on the significantly higher viscosity of the 4× complex compared to the 2× complex, drug release is slower from the higher concentration complex. Thus, by changing the concentration of the polymers within the complex, the rate of drug release can be increased or decreased as desired based on the relative effects of the complex viscosity, the intermolecular complex strength, and the osmotic driving force for complex swelling. Mixing different anionic polymers together which have different properties in this regard may then yield complexes with tunable release kinetics based on the average properties of the anionic polymer solution used.

Figure 21:
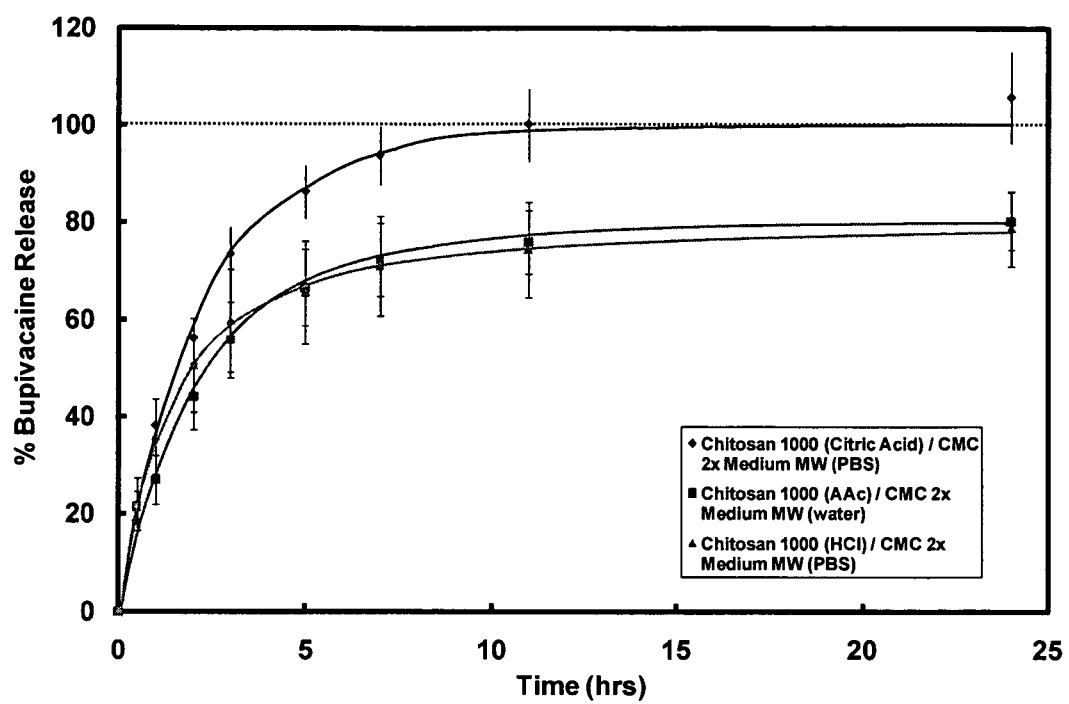
Figure 22:
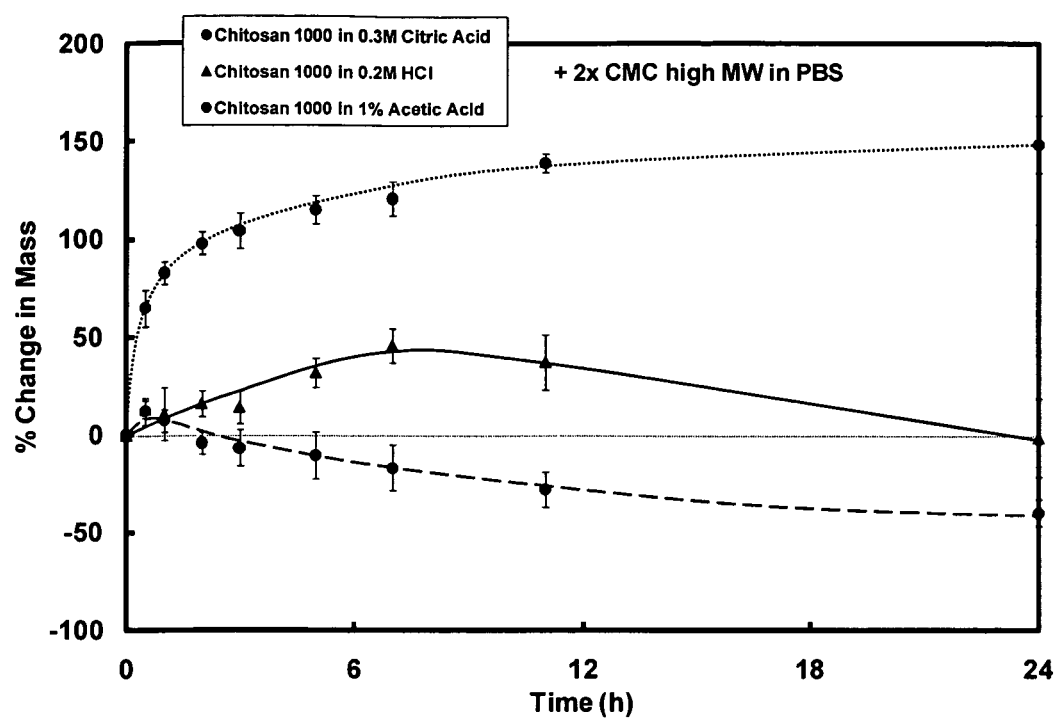

Effect of Chitosan Solution: To see if the acid solution used to dissolve the chitosan (cationic) phase of the polyelectrolyte complexes significantly changes the swelling and drug delivery properties of the complexes, we prepared the 3 wt % chitosan solutions used for the analysis in 0.3 M acetic acid, 0.2 M hydrochloric acid, or a pH 4 0.3 M citric acid buffer solutions and assayed the physicochemical and biological properties of the resulting complexes. FIG. 21 shows the drug release properties of the different chitosan solution complexes prepared with 6 wt % high molecular weight carboxymethyl cellulose dissolved in PBS, while FIG. 22 shows the swelling responses of the same complexes over time.

Complexes prepared from chitosan dissolved in citric acid exhibit a large swelling response over time and correspondingly release drug much faster than complexes prepared with hydrochloric acid or acetic acid, both of which exhibited relatively small degrees of swelling or de-swelling over time and released drug more slowly at approximately the same rate. Citric acid is a multivalent anion and as such may increase the Donnan equilibrium-based driving force for complex swelling due to charge interactions. Hence, hydrochloric acid and acetic acid appear to be better choices from a physicochemical perspective for preparing the complexes.

Figure 23:
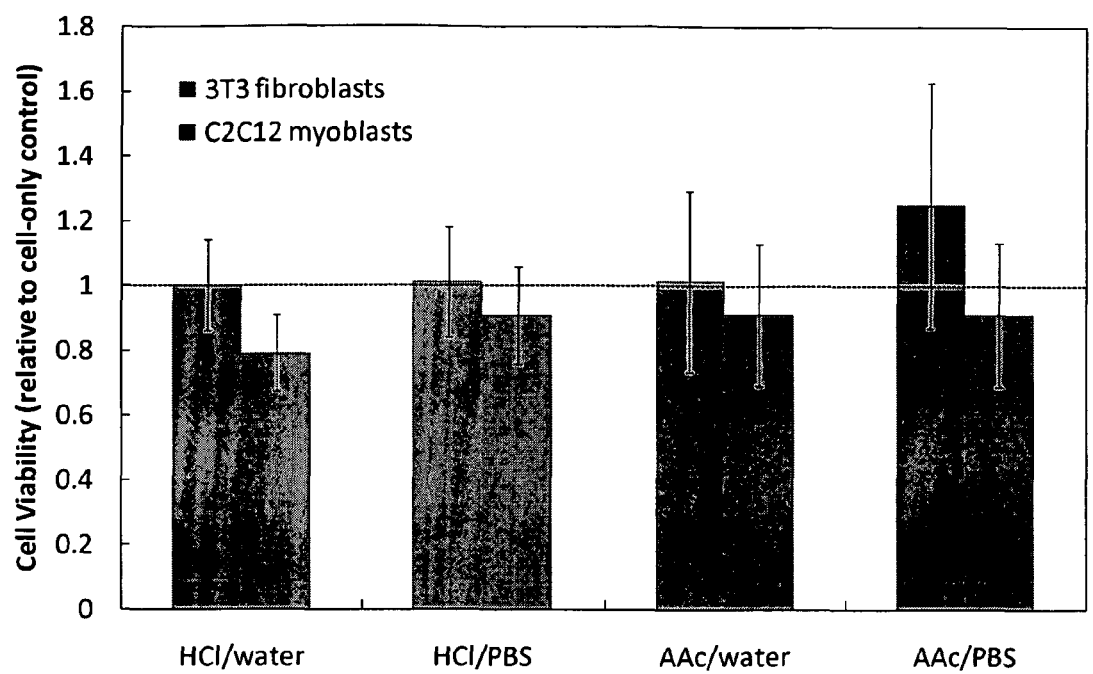

To determine the biological efficacy of such formulations, we evaluated the cytotoxicity of polyelectrolyte complexes prepared using both acidic solvents to C2C12 myoblasts and 3T3 fibroblasts using the MTT cell proliferation assay, the results of which are shown in FIG. 23.

FIG. 23 indicates that both hydrochloric acid and acetic acid can be used to create complexes which exhibit good biocompatibility when assessed in vitro. Complexes based on chitosan dissolved in either acidic solution and carboxymethyl cellulose dissolved in water showed no significant cytotoxicity compared to the cell-only control, while only minimal cytotoxicity was noted for the chitosan in HCl/CMC in water complex. This minor cytotoxic response is likely due to the reduction in complex buffering capacity upon mixing the strong acid HCl with water instead of PBS, which would moderate the acidic pH of the overall complex. Thus, for the chitosan used primarily in the study, using either hydrochloric acid or acetic acid as the chitosan carrying phase and phosphate-buffered saline as the anionic polymer carrying phase appears to offer both the best drug delivery properties as well as the mildest cytotoxicity response.

Figure 24:
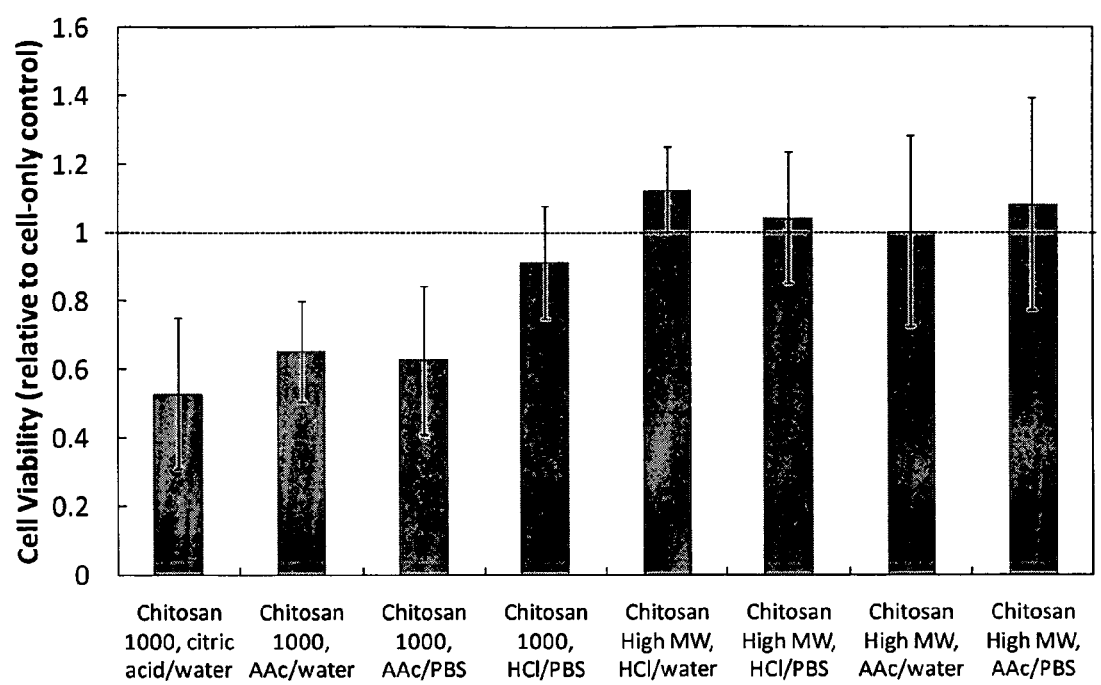

However, it must be noted that this result can vary depending on the source of the chitosan used to prepare the complexes. FIG. 24 shows the cell viability of 3T3 fibroblasts when exposed to chitosan-carboxymethylcellulose complexes made from two different chitosan sources: chitosan 1000 distributed by Wako Chemicals and high molecular weight chitosan (from clam shells) distributed by Sigma-Aldrich. Both chitosans are considered "high" molecular weight by their manufacturers and produce solutions of similar viscosity when dissolved in either acid solution.

Chitosan 1000-based complexes induce significant cytotoxicity when dissolved in citric acid or acetic acid (even when buffered with PBS), but exhibit good biocompatibility when hydrochloric acid is used to dissolve the chitosan and PBS is used to dissolve the carboxymethyl cellulose. As noted previously, this combination will provide the most effective buffering of the acidic chitosan solution inside the resulting polyelectrolyte complex, potentially explaining its optimally biocompatibility. However, when the Sigma-Aldrich high molecular weight chitosan from clam shells is used, all combinations of solvents give biocompatible complexes. This difference in biocompatibility based on chitosan source is likely a result of the different impurities resulting from the different methods used to extract chitosan by different suppliers and may explain (at least in part) the varying reports on the efficacy and biological inertness of chitosan and chitosan-based implants for in vivo use. Hence, the source of chitosan may be important for safe clinical use of polyelectrolyte complex-based drug delivery vehicles.

Figure 25:
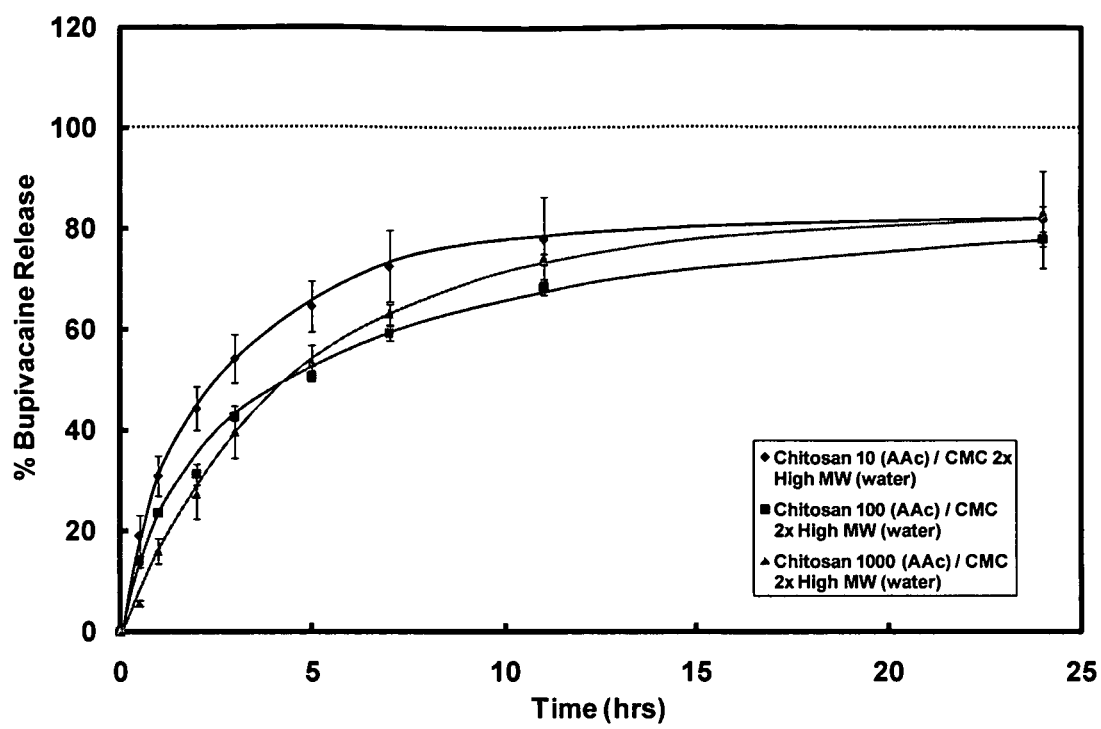
Figure 26:
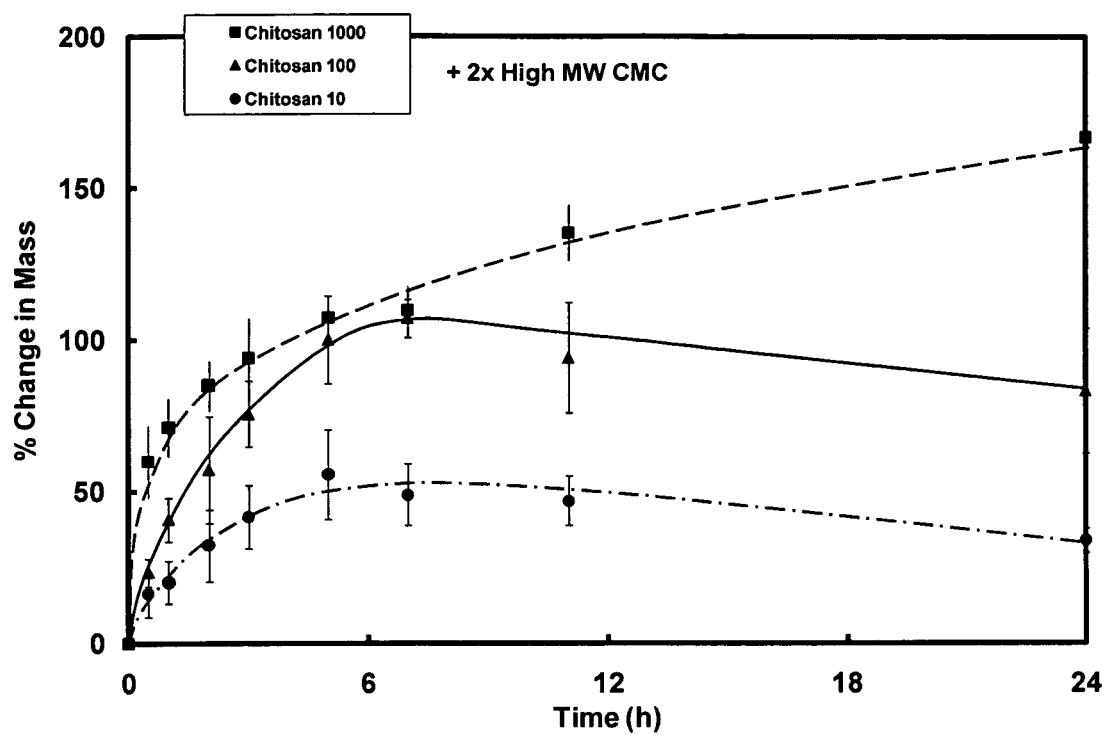
FIG. 26. Percentage mass change of polyelectrolyte complexes of chitosan of various molecular weight (dissolved in acetic acid) and high molecular weight carboxymethyl cellulose (dissolved in water).

Effect of Polymer Molecular Weight: FIG. 25 shows the drug delivery properties of chitosan-high molecular weight carboxymethyl cellulose complexes prepared using chitosans of different molecular weights, while FIG. 26 shows the corresponding swelling properties of the complexes evaluated. Chitosan 10 is low molecular weight, chitosan 100 is medium molecular weight, and chitosan 1000 is high molecular weight.

Chitosan-CMC is a relatively weaker interacting polyelectrolyte pair such that, based on the results discussed in FIGS. 19 and 20, ionic crosslinking is likely to be less important than osmotic and viscous effects in regulating drug release. FIGS. 25 and 26 indicate this is indeed the case as the chitosan molecular weight is changed. Complexes prepared with low molecular weight chitosan swell the least but are also the least viscous so release drug faster than complexes prepared with higher molecular weight chitosans. Medium molecular weight chitosan 100 also clearly releases drug faster than the high molecular weight chitosan 1000 in the early stages of the release experiment but then slows down to a release rate slightly below that of the high molecular weight chitosan at the later stages of release. This phenomenon is likely attributable to the observation that chitosan 100 starts to deswell at longer time points while the high molecular weight chitosan 1000 complex continues to swell over the full time period tested, impacting the relative diffusion resistances to drug delivery from each of the complexes.

Figure 27:
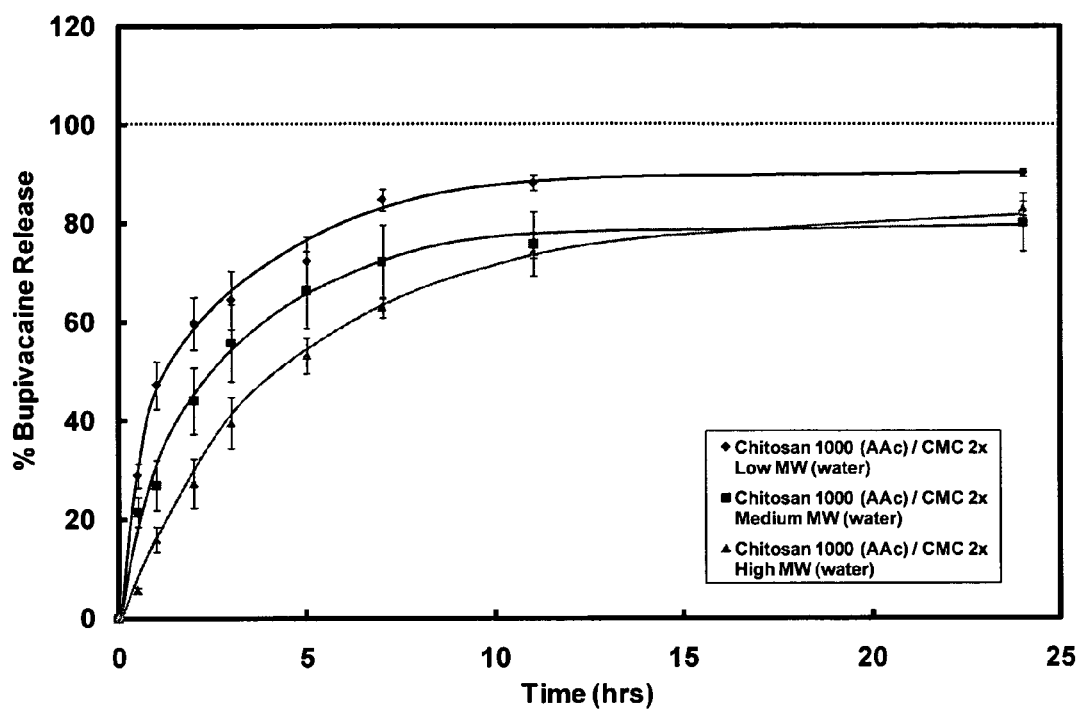
FIG. 27. Bupivacaine release kinetics of polyelectrolyte complexes of high molecular weight chitosan 1000 (dissolved in acetic acid) and carboxymethyl cellulose of varying molecular weight (dissolved in water).
Figure 28:
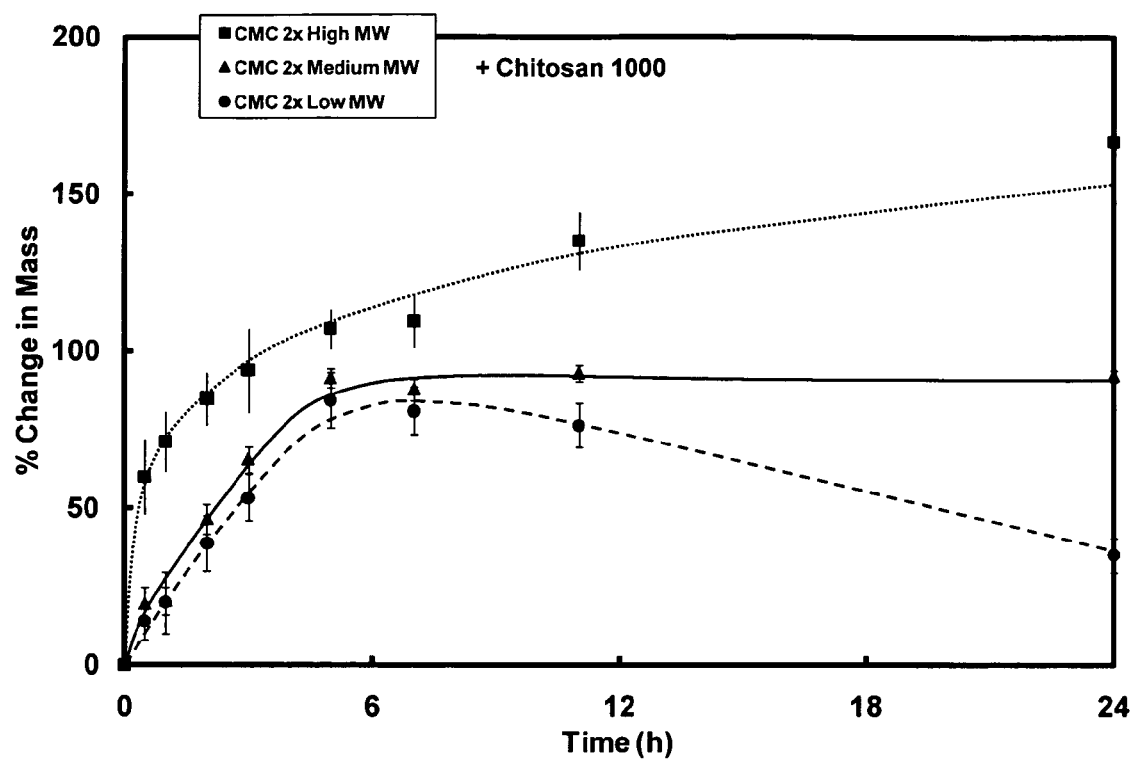
FIG. 28. Percentage mass change of polyelectrolyte complexes of high molecular weight chitosan 1000 (dissolved in acetic acid) and carboxymethyl cellulose of varying molecular weight (dissolved in water).

Similar results can be achieved when the molecular weight of the anionic polymer is varied. FIG. 27 shows the drug delivery properties of chitosan 1000 (high molecular weight)-carboxymethyl cellulose complexes prepared using carboxymethyl celluloses of different molecular weights, while FIG. 28 shows the corresponding swelling properties of the complexes evaluated.

As with chitosan, complexes made using low molecular weight carboxymethyl cellulose swell the least but also release drug fastest due to the lower overall viscosity (i.e. lower resistance to drug diffusion) of the complex. As the molecular weight of the CMC used increased, the complexes continue to swell to a larger degree but also become significantly more viscous, releasing the drug more slowly (i.e., the high molecular weight CMC complex provides the slowest drug release). Thus, the release rate of drug from the polyelectrolyte complexes can be controlled by varying the molecular weight of either of the constituent polymers.

Example 4

Exemplary Gel Drops

Two examples of gel drops that can be applied to the ear canal as a liquid, and subsequently gel to form a stable reservoir on the surface of the tympanic membrane (TM), or eardrum, are:
1) 18% Poloxamer 407 (P407) in a 1% ciprofloxacin solution
2) 12% chitosan (Ch), 12% chondroitin sulfate (CS) in a 1% ciprofloxacin solution The two formulations can be prepared with or without various individual or combination chemical penetration enhancers (CPEs), e.g., sodium lauryl sulfate (SLS) and limonene. The amino amide local anesthetic bupivacaine can also be included, and has been found to further enhance permeant flux.

We have prepared these formulations with various model permeants (e.g., ciprofloxacin, cefuroxime, levofloxacin) and tested them in vitro in human skin models and chinchilla TM models. We have also applied the gel drops to chinchilla TMs in vivo in order to assess the effect of the drops on hearing thresholds. The table below summarizes some basic properties and threshold effects of the two formulations.

|  | Gelation time @ 35° C. | Gelation mechanism | Tested and combatible with following CPEs | Measured effects on auditory thresholds |
| --- | --- | --- | --- | --- |
| 18% P407 | <30 seconds | Reverse thermal gelation due to micelle formation | Anionic surfactants (SLS), terpenes (limonene), amino amides (bupivacaine) | No effect with 100 uL volume on TM |
| 12% Ch/CS | 60 seconds | Polyelectrolyte complex formation | Anionic surfactants (SLS), terpenes (limonene), amino amides (bupivacaine) | 10 dB threshold increase with 100 uL volume on TM |

We have demonstrated in vitro that both formulations provide sustained release of the selected permeant (e.g., ciprofloxacin) out of the gel carrier and across the TM. A recent in vivo experiment also suggested efficacy by eradicating *Haemophilus influenzae* in a chinchilla model of otitis media (OM); three of four animals with OM were cleared of infection (*H. influenzae* count down to zero) within 3 days of a single drop application, and the median bacteria count in the four animal group decreased from $2.6 \times 10^5$ to $5.0 \times 10^1$, versus a hundred-fold increase in the no-treatment control group.

It is to be understood that the mode of treatment is not limited to the polymers, mechanisms of gelation, antimicrobial permeants, or the CPEs discussed herein. It is applicable to any liquid with in-situ gelation capabilities, any CPEs compatible with the chosen mechanism, and any small molecule therapy relevant to middle ear disease.

REFERENCES

All references cited are hereby incorporated herein by reference.
1. Casselbrant, M. L. and E. M. Mandel, Genetic susceptibility to otitis media. Curr Opin Allergy Clin Immunol, 2005. 5(1): p. 1-4.
2. Casselbrant, M. L. and E. M. Mandel, The genetics of otitis media. Curr Allergy Asthma Rep, 2001. 1(4): p. 353-7.
3. Berman, S., Management of acute and chronic otitis media in pediatric practice. Curr Opin Pediatr, 1995. 7(5): p. 513-22.
4. Freid, V. M., D. M. Makuc, and R. N. Rooks, Ambulatory health care visits by children: principal diagnosis and place of visit. Vital Health Stat 13, 1998(137): p. 1-23.
5. Hoffman, R. A. and C. L. Li, Tetracaine topical anesthesia for myringotomy. Laryngoscope, 2001. 111(9): p. 1636-8.
6. Alvarez-Roman, R., et al., Skin permeability enhancement by low frequency sonophoresis: lipid extraction and transport pathways. J Pharm Sci, 2003. 92(6): p. 1138-46.
7. Hasegawa, M., Y. Saito, and I. Watanabe, Iontophoretic anaesthesia of the tympanic membrane. Clin Otolaryngol Allied Sci, 1978. 3(1): p. 63-6.
8. Karande, P., et al., Design principles of chemical penetration enhancers for transdermal drug delivery. Proc Natl Acad Sci USA, 2005. 102(13): p. 4688-93.
9. Takats, Z., K. Vekey, and L. Hegedus, Qualitative and quantitative determination of poloxamer surfactants by mass spectrometry. Rapid Commun Mass Spectrom, 2001. 15(10): p. 805-10.
10. Ruel-Gariepy, E. and J. C. Leroux, In situ-forming hydrogels—review of temperaturesensitive systems. Eur J Pharm Biopharm, 2004. 58(2): p. 409-26.
11. Ruel-Gariepy, E., et al., A thermosensitive chitosan-based hydrogel for the local delivery of paclitaxel. Eur J Pharm Biopharm, 2004. 57(1): p. 53-63.
12. Chen, W. B., et al., Characterization of polyelectrolyte complexes between chondroitin sulfate and chitosan in the solid state. J Biomed Mater Res A, 2005. 75(1): p. 128-37.
13. Salyers, A. A. and M. O'Brien, Cellular location of enzymes involved in chondroitin sulfate breakdown by Bacteroides thetaiotaomicron. J Bacteriol, 1980. 143(2): p. 772-80.
14. Morreale, P., et al., Comparison of the antiinflammatory efficacy of chondroitin sulfate and diclofenac sodium in patients with knee osteoarthritis. J Rheumatol, 1996. 23(8): p. 1385-91.
15. Ronca, F., et al., Anti-inflammatory activity of chondroitin sulfate. Osteoarthritis Cartilage, 1998. 6 Suppl A: p. 14-21.
16. Lovdahl, M., et al., Determination of ciprofloxacin levels in chinchilla middle ear effusion and plasma by high-performance liquid chromatography with fluorescence detection. J Chromatogr, 1993. 617(2): p. 329-33.
17. Yong, C. S., et al., Effect of sodium chloride on the gelation temperature, gel strength and bioadhesive force of poloxamer gels containing diclofenac sodium. Int J Pharm, 2001. 226(1-2): p. 195-205.
18. Ryu, J. M., et al., Increased bioavailability of propranolol in rats by retaining thermally gelling liquid suppositories in the rectum. J Control Release, 1999. 59(2): p. 163-72.
19. Choi, H., et al., Effect of additives on the physicochemical properties of liquid suppository bases. Int J Pharm, 1999. 190(1): p. 13-9.
20. Magnuson, K. and S. Hellstrom, Early structural changes in the rat tympanic membrane during pneumococcal otitis media. Eur Arch Otorhinolaryngol, 1994. 251(7): p. 393-8.
21. Krueger, G. G., et al., The development of a rat/human skin flap served by a defined and accessible vasculature on a congenitally athymic (nude) rat. Fundam Appl Toxicol, 1985. 5(6 Pt 2): p. S112-21.
22. Merchant, S. N., et al., Analysis of middle ear mechanics and application to diseased and reconstructed ears. Am J Otol, 1997. 18(2): p. 139-54.
23. Merchant, S. N., J. J. Rosowski, and M. E. Ravicz, Middle ear mechanics of type IV and type V tympanoplasty: II. Clinical analysis and surgical implications. Am J Otol, 1995. 16(5): p. 565-75.
24. Rosowski, J. J., et al., Cadaver middle ears as models for living ears: comparisons of middle ear input immittance. Ann Otol Rhinol Laryngol, 1990. 99(5 Pt 1): p. 403-12.
25. Rosowski, J. J., S. N. Merchant, and M. E. Ravicz, Middle ear mechanics of type IV and type V tympanoplasty: I. Model analysis and predictions. Am J Otol, 1995. 16(5): p. 555-64.

26. Voss, S. E., et al., Acoustic responses of the human middle ear. Hear Res, 2000. 150(1-2): p. 43-69.

It will be clear that the invention may be practiced other than as particularly described in the foregoing description and examples. Numerous modifications and variations of the present disclosure are possible in light of the above teachings and, therefore, are within the scope of the claims. Preferred features of each aspect of the disclosure are as for each of the other aspects mutatis mutandis. The documents including patents, patent applications, journal articles, or other disclosures mentioned herein are hereby incorporated by reference in their entirety. In the event of conflict, the disclosure of the present application controls, other than in the event of clear error.

What is claimed is:

1. A composition for treating otitis media comprising:
   a. a therapeutic agent, wherein the therapeutic agent is selected from the group consisting of ciprofloxacin, cefuroxime, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, enoxacin, gatifloxacin, levofloxacin, lomefloxacin, moxifloxacin, norfloxacin, ofloxacin, trovafloxacin, bacitracin, colistin, polymyxin B, azithromycin, clarithromycin, dirithromycin, erythromycin, roxithromycin, troleandomycin, telithromycin, spectinomycin, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, mafenide, sulfacetamide, sulfamethizole, sulfasalazine, sulfisoxazole, trimethoprim, and trimethoprim-sulfamethoxazole;
   b. a penetration enhancer, wherein the penetration enhancer is a combination of bupivacaine, limonene, and sodium dodecyl sulfate; and
   c. a sustained release drug delivery agent, wherein the sustained release drug delivery agent is a matrix forming agent.

2. The composition of claim 1 further comprising another therapeutic agent.

3. The composition of claim 1 wherein the matrix forming agent is selected from the group consisting of polyelectrolyte complexes, thermo-responsive gelling agents, pre-polymers, alginates, un-crosslinked polymers, and monomers.

4. The composition of claim 1 wherein the matrix forming agent is a polyelectrolyte complex comprising chitosan, as a cationic component, and one of chondroitin sulfate, dextran sulfate, hyaluronic acid, alginic acid, or carboxymethyl cellulose, as an anionic component.

5. The composition of claim 1 wherein the matrix forming agent is selected from the group consisting of chitosan-chondroitin sulfate, chitosan-dextran sulfate, chitosan-hyaluronic acid, chitosan-alginic acid, and chitosan-carboxymethylcellulose.

6. The composition of claim 1 wherein the matrix forming agent is selected from a group consisting of poloxamer 407, poloxamer 188, poloxamines, methylcellulose, hydroxypropyl methylcellulose, ethyl (hydroxy ethyl) cellulose, xyloglucan, celluose acetate phthalate latex, poly (acrylic acid), and gellan gum.

7. The composition of claim 1, wherein the matrix forming agent is biocompatible.

8. The composition of claim 1, wherein the matrix forming agent is biodegradable.

9. The composition of claim 1, wherein the penetration enhancer is about 0.1 to about 10 percent of the composition.

10. The composition of claim 1, comprising 0.5% bupivacaine, about 2% limonene, and about 1% sodium dodecyl sulfate.

11. A method of treating a subject with otitis media comprising administering to the subject a composition comprising:
   a. a therapeutic agent, wherein the therapeutic agent is selected from the group consisting of ciprofloxacin, cefuroxime, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, enoxacin, gatifloxacin, levofloxacin, lomefloxacin, moxifloxacin, norfloxacin, ofloxacin, trovafloxacin, bacitracin, colistin, polymyxin B, azithromycin, clarithromycin, dirithromycin, erythromycin, roxithromycin, troleandomycin, telithromycin, spectinomycin, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, mafenide, sulfacetamide, sulfamethizole, sulfasalazine, sulfisoxazole, trimethoprim, and trimethoprim-sulfamethoxazole;
   b. a penetration enhancer, wherein the penetration enhancer is a combination of bupivacaine, limonene, and sodium dodecyl sulfate; and
   c. a sustained release drug delivery agent, wherein the sustained release drug delivery agent is a matrix forming agent.

* * * * *